(12) United States Patent
Gewehr et al.

(10) Patent No.: US 8,748,339 B2
(45) Date of Patent: Jun. 10, 2014

(54) SYNERGISTIC FUNGICIDAL MIXTURES

(75) Inventors: Markus Gewehr, Kastellaun (DE); Jochen Dietz, Karlsrhue (DE); Thomas Grote, Wachenheim (DE); Egon Haden, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 507 days.

(21) Appl. No.: 12/996,040

(22) PCT Filed: Jun. 4, 2009

(86) PCT No.: PCT/EP2009/056866
§ 371 (c)(1),
(2), (4) Date: Dec. 3, 2010

(87) PCT Pub. No.: WO2009/147205
PCT Pub. Date: Dec. 10, 2009

(65) Prior Publication Data
US 2011/0177944 A1    Jul. 21, 2011

(30) Foreign Application Priority Data
Jun. 5, 2008    (EP) ..................................... 08157648

(51) Int. Cl.
*A01N 43/56* (2006.01)
*A01N 43/54* (2006.01)
*A01N 43/40* (2006.01)
*A01P 3/00* (2006.01)

(52) U.S. Cl.
USPC ........ 504/100; 514/404; 514/407; 514/229.2; 514/269; 514/345; 514/357; 514/531; 514/539; 514/619; 514/620

(58) Field of Classification Search
USPC .............. 514/407, 404, 229.2, 269, 345, 357, 514/531, 539, 619, 620; 504/100
See application file for complete search history.

(56) References Cited

FOREIGN PATENT DOCUMENTS

| | | |
|---|---|---|
| EP | 1 072 598 | 1/2001 |
| EP | 1 222 856 | 7/2002 |
| EP | 1 652 429 | 5/2006 |
| WO | WO 2009/119872 | 10/2009 |
| WO | WO 2009/119873 | 10/2009 |

OTHER PUBLICATIONS

International Search Report for International Application No. PCT/EP2009/056866, dated Apr. 2010.
International Preliminary Report on Patentability for International Application No. PCT/EP2009/056866, dated Dec. 2010.

*Primary Examiner* — John Pak
(74) *Attorney, Agent, or Firm* — Brinks Gilson Lione

(57) ABSTRACT

The present invention relates to a composition, comprising a 5-amino-3-oxo-2,3-dihydro-pyrazole of the formula I as defined in the claims and the description and at least one active compound II selected from groups A) to I) in a synergistically effective amount.

16 Claims, No Drawings

SYNERGISTIC FUNGICIDAL MIXTURES

This application is a National Stage application of International Application No. PCT/EP2009/056866 filed Jun. 4, 2009, the entire contents of which is hereby incorporated herein by reference. This application also claims priority under 35 U.S.C. §119 to European Patent Application No. 08157648.0, filed Jun. 5, 2008, the entire contents of which is hereby incorporated herein by reference.

DESCRIPTION

The present invention relates to compositions comprising as active components
1) a 5-amino-3-oxo-2,3-dihydro-pyrazole of the formula I

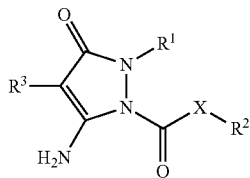

wherein
$R^1$ is $C_1$-$C_{10}$-alkyl;
$R^2$ is $C_1$-$C_6$-alkyl, $C_2$-$C_6$-alkenyl or $C_2$-$C_6$-alkynyl;
$R^3$ is aryl, optionally substituted by one to five substituents independently selected from the group consisting of halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_6$-alkyl, $C_1$-$C_6$-alkoxy-$C_1$-$C_6$-alkoxy, $C_1$-$C_6$-alkylthio, $C_1$-$C_6$-haloalkylthio, $C_2$-$C_6$-alkenylthio, $C_2$-$C_6$-haloalkenylthio, cyano and nitro; and
X is O or S;
and
2) at least one active compound II selected from groups A) to I):

A) Strobilurins
  azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxy-imino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-di-chlorophenyl)-1-methyl-allylidene-aminooxymethyl)-phenyl)-2-methoxyimino-N-methyl-acetamide;

B) Carboxamides
  carboxanilides: benalaxyl, benalaxyl-M, benodanil, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, tecloftalam, thifluzamide, tiadinil, 2-amino-4-methyl-thiazole-5-carboxanilide, 2-chloro-N-(1,1,3-trimethyl-indan-4-yl)-nicotinamide, N-(2',4'-difluorobiphenyl-2-yl)-3-difluoromethyl-1-methyl-1H-pyrazole-4-carboxamide, N-(2',4'-dichlorobiphenyl-2-yl)-3-difluoromethyl-1-methyl-1H-pyrazole-4-carboxamide, N-(2',5'-difluorobiphenyl-2-yl)-3-difluoromethyl-1-methyl-1H-pyrazole-4-carboxamide, N-(2',5'-dichlorobiphenyl-2-yl)-3-difluoromethyl-1-methyl-1H-pyrazole-4-carboxamide, N-(3',5'-difluorobiphenyl-2-yl)-3-difluoromethyl-1-methyl-1H-pyrazole-4-carboxamide, N-(3'-fluorobiphenyl-2-yl)-3-difluoromethyl-1-methyl-1H-pyrazole-4-carboxamide, N-(3'-chlorobiphenyl-2-yl)-3-difluoromethyl-1-methyl-1H-pyrazole-4-carboxamide, N-(2'-fluorobiphenyl-2-yl)-3-difluoromethyl-1-methyl-1H-pyrazole-4-carboxamide, N-(2'-chlorobiphenyl-2-yl)-3-difluoromethyl-1-methyl-1H-pyrazole-4-carboxamide, N-(3',5'-dichlorobiphenyl-2-yl)-3-difluoromethyl-1-methyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[2-(1,1,2,2-tetrafluoroethoxy)-phenyl]-3-difluoromethyl-1-methyl-1H-pyrazole-4-carboxamide, N-(4'-trifluoromethylthiobiphenyl-2-yl)-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide, N-(2-(1,3,3-trimethyl-butyl)-phenyl)-1,3-dimethyl-5-fluoro-1H-pyrazole-4-carboxamide, N-(4'-chloro-3',5'-difluoro-biphenyl-2-yl)-3-difluoromethyl-1-methyl-1H-pyrazole-4-carboxamide, N-(4'-chloro-3',5'-difluoro-biphenyl-2-yl)-3-trifluoromethyl-1-methyl-1H-pyrazole-4-carboxamide, N-(3',4'-dichloro-5'-fluoro-biphenyl-2-yl)-3-trifluoromethyl-1-methyl-1H-pyrazole-4-carboxamide, N-(3',5'-difluoro-4'-methyl-biphenyl-2-yl)-3-difluoromethyl-1-methyl-1H-pyrazole-4-carboxamide, N-(3',5'-difluoro-4'-methyl-biphenyl-2-yl)-3-trifluoromethyl-1-methyl-1H-pyrazole-4-carboxamide, N-(2-bicyclopropyl-2-yl-phenyl)-3-difluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide, N-[1,2,3,4-tetrahydro-9-(1-methylethyl)-1,4-methano-naphthalen-5-yl]-3-(difluoromethyl)-1-methyl-1H-pyrazole-4-carboxamide;

carboxylic morpholides: dimethomorph, flumorph;
benzoic acid amides: flumetover, fluopicolde, fluopyram, zoxamide, N-(3-ethyl-3,5-5trimethylcyclohexyl)-3-formylamino-2-hydroxybenzamide;
other carboxamides: carpropamid, dicyclomet, mandiproamid, oxytetracyclin, silthiofarm and N-(6-methoxy-pyridin-3-yl)cyclopropanecarboxylic acid amide;

C) Azoles
  triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chloro-phenyl)-2-([1,2,4]triazol-1-yl)-cycloheptanol;
  imidazoles: cyazofamid, imazalil, pefurazoate, prochloraz, triflumizol;
  benzimidazoles: benomyl, carbendazim, fuberidazole, thiabendazole;
  others: ethaboxam, etridiazole, hymexazole and 2-(4-chloro-phenyl)-N-[4-(3,4-di-methoxy-phenyl)-isoxazol-5-yl]-2-prop-2-ynyloxy-acetamide;

D) Heterocyclic Compounds
  pyridines: pyrifenox, 3-[5-(4-chloro-phenyl)-2,3-dimethyl-isoxazolidin-3-yl]-pyridine, 3-[5-(4-methyl-phenyl)-2,3-dimethyl-isoxazolidin-3-yl]-pyridine, 2,3,5,6-tetra-chloro-4-methanesulfonyl-pyridine, 3,4,5-trichloropyridine-2,6-di-carbonitrile, N-(1-(5-bromo-3-chloro-pyridin-2-yl)-ethyl)-2,4-dichloronicotinamide, N-[(5-bromo-3-chloro-pyridin-2-yl)-methyl]-2,4-dichloro-nicotinamide;
  pyrimidines: bupirimate, diflumetorim, fenarimol, ferimzone, nitrapyrin, nuarimol;
  piperazines: triforine;
  pyrroles: fenpiclonil;
  morpholines: aldimorph, dodemorph, dodemorph-acetate, fenpropimorph, tridemorph;
  piperidines: fenpropidin;
  dicarboximides: fluoroimid;
  non-aromatic 5-membered heterocycles: famoxadone, fenamidone, octhilinone, probenazole;
  others: acibenzolar-5-methyl, amisulbrom, anilazin, blasticidin-S, captafol, captan, chinomethionat, dazomet, debacarb, diclomezine, difenzoquat, difenzoquat-methylsulfate, fenoxanil, Folpet, oxolinic acid, piperalin, proquinazid, pyroquilon, quinoxyfen, triazoxide, tricyclazole, 2-butoxy-6-iodo-3-propylchromen-4-one, 5-chloro-1-(4,6-dimethoxy-pyrimidin-2-yl)-2-methyl-1H-benzoimidazole, 5-chloro-7-(4-methylpiperidin-1-yl)-6-(2,4,6-trifluorophenyl)-[1,2,4]triazolo[1,5-a]pyrimidine, 6-(3,4-dichloro-phenyl)-5-methyl-[1,2,4]triazolo[1,5-a]pyrimidine-7-ylamine, 6-(4-tert-butyl-phenyl)-5-methyl-[1,2,4]triazolo[1,5-a]pyrimidine-7-ylamine, 5-methyl-6-(3,5,5-tri-methyl-hexyl)-[1,2,4]triazolo[1,5-a]pyrimidine-7-ylamine, 5-methyl-6-octyl-[1,2,4]triazolo[1,5-a]pyrimidine-7-ylamine, 6-methyl-5-octyl-[1,2,4]triazolo[1,5-a]pyrimidine-7-ylamine, 6-ethyl-5-octyl-[1,2,4]triazolo[1,5-a]pyrimidine-7-ylamine, 5-ethyl-6-octyl-[1,2,4]triazolo[1,5-a]pyrimidine-7-ylamine, 5-ethyl-6-(3,5,5-trimethyl-hexyl)-[1,2,4]triazolo[1,5-a]pyrimidine-7-ylamine, 6-octyl-5-propyl-[1,2,4]triazolo[1,5-a]pyrimidine-7-ylamine, 5-methoxymethyl-6-octyl-[1,2,4]triazolo[1,5-a]pyrimidine-7-ylamine, 6-octyl-5-trifluoromethyl-[1,2,4]triazolo[1,5-a]pyrimidine-7-ylamine and 5-trifluoro-methyl-6-(3,5,5-trimethyl-hexyl)-[1,2,4]triazolo[1,5-a]pyrimidine-7-ylamine;
E) Carbamates
  thio- and dithiocarbamates: ferbam, mancozeb, maneb, metam, methasulphocarb, metiram, propineb, thiram, zineb, ziram;
  carbamates: benthiavalicarb, flubenthiavalicarb, iprovalicarb, propamocarb, propamocarb hydrochlorid, valiphenal and N-(1-(1-(4-cyano-phenyl)ethanesulfonyl)-but-2-yl) carbamic acid-(4-fluorophenyl) ester;
F) Other Active Substances
  guanidines: guanidine, dodine, dodine free base, guazatine, guazatine-acetate, iminoctadine, iminoctadine-triacetate, iminoctadine-tris(albesilate);
  antibiotics: kasugamycin, kasugamycin hydrochloride-hydrate, streptomycin, polyoxine, validamycin A;
  nitrophenyl derivates: binapacryl, dinobuton, dinocap, nitrthal-isopropyl, tecnazen;
  organometal compounds: fentin salts, such as fentin-acetate, fentin chloride or fentin hydroxide;
  sulfur-containing heterocyclyl compounds: dithianon, isoprothiolane;
  organophosphorus compounds: edifenphos, fosetyl, fosetyl-aluminum, iprobenfos, phosphorous acid and its salts, pyrazophos, tolclofos-methyl;
  organochlorine compounds: chlorothalonil, dichlofluanid, dichlorophen, flusulfamide, hexachlorobenzene, pencycuron, pentachlorphenole and its salts, phthalide, quintozene, thiophanate-methyl, tolylfluanid, N-(4-chloro-2-nitro-phenyl)-N-ethyl-4-methyl-benzenesulfonamide;
  inorganic active substances: Bordeaux mixture, copper acetate, copper hydroxyide, copper oxychloride, basic copper sulfate, sulfur;
  others: biphenyl, bronopol, cyflufenamid, cymoxanil, diphenylamin, metrafenone, mildiomycin, oxin-copper, prohexadione-calcium, spiroxamine, tolylfluanid, N-(cyclo-propylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-propoxy)-phenyl)-N-ethyl-N-methyl formamidine and N'-(5-difluoromethyl-2-methyl-4-(3-trimethylsilanyl-propoxy)-phenyl)-N-ethyl-N-methyl formamidine;
G) Growth Regulators
  abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;
H) Herbicides
  acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
  amino acid derivatives: bilanafos, glyphosate, glufosinate, sulfosate;
  aryloxyphenoxypropionates: clodinafop, cyhalofop-butyl, fenoxaprop, fluazifop, haloxyfop, metamifop, propaquizafop, quizalofop, quizalofop-P-tefuryl;
  Bipyridyls: diquat, paraquat;
  (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
  cyclohexanediones: butroxydim, clethodim, cycloxydim, profoxydim, sethoxydim, tepraloxydim, tralkoxydim;
  dinitroanilines: benfluralin, ethalfluralin, oryzalin, pendimethalin, prodiamine, trifluralin;
  diphenyl ethers: acifluorfen, aclonifen, bifenox, diclofop, ethoxyfen, fomesafen, lactofen, oxyfluorfen;
  hydroxybenzonitriles: bomoxynil, dichlobenil, ioxynil;
  imidazolinones: imazamethabenz, imazamox, imazapic, imazapyr, imazaquin, imazethapyr;
  phenoxy acetic acids: clomeprop, 2,4-dichlorophenoxy-acetic acid (2,4-D), 2,4-DB, dichlorprop, MCPA, MCPA-thioethyl, MCPB, Mecoprop;
  pyrazines: chloridazon, flufenpyr-ethyl, fluthiacet, norflurazon, pyridate;

pyridines: aminopyralid, clopyralid, diflufenican, dithiopyr, fluridone, fluoroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bromacil, bromobutide, butafenacil, butamifos, cafenstrole, carfentrazone, cinidon-ethlyl, chlorthal, cinmethylin, clomazone, cumyluron, cyprosulfamide, dicamba, difenzoquat, diflufenzopyr, *Drechslera monoceras*, endothal, ethofumesate, etobenzanid, fentrazamide, flumiclorac-pentyl, flumioxazin, flupoxam, fluorochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, 4-hydroxy-3-[2-(2-methoxyethoxymethyl)-6-trifluoromethyl-pyridine-3-carbonyl]-bicyclo[3.2.1]oct-3-en-2-one, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoropyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester;

I) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluoron, and pyrifluquinazon.

in a synergistically effective amount.

Moreover, the invention relates also to a method for controlling phytopathogenic harmful fungi using mixtures of a compound of formula I and an active compound II and to the use of compounds I and compounds II for preparing such mixtures, and to compositions and seed comprising these mixtures.

Practical agricultural experience has shown that the repeated and exclusive application of an individual active compound in the control of harmful fungi leads in many cases to a rapid selection of those fungus strains which have developed natural or adapted resistance against the active compound in question. Effective control of these fungi with the active compound in question is then no longer possible.

To reduce the risk of the selection of resistant fungus strains, mixtures of different active compounds are nowadays conventionally employed for controlling harmful fungi. By combining active compounds having different mechanisms of action, it is possible to ensure successful control over a relatively long period of time.

It is an object of the present invention to provide, with a view to effective resistance management and effective control of phytopathogenic harmful fungi, at application rates which are as low as possible, compositions which, at a reduced total amount of active compounds applied, have improved activity against the harmful fungi (synergistic mixtures) and a broadened activity spectrum, in particular for certain indications.

We have accordingly found that this object is achieved by the compositions, defined herein, comprising at least one compound I and at least one compound II. Moreover, we have found that simultaneous, that is joint or separate, application of at least one compound I and at least one compound II or successive application of a compound I and of a compound II allows better control of harmful fungi than is possible with the individual compounds alone (synergistic mixtures). Furthermore, synergistic effects in relation with the insecticidal and/or herbicidal action has been found with the inventive compositions.

The composition according to the invention may be a (physical) mixture of the compound I and the at least one compound II. Accordingly, the invention also provides a mixture comprising one compound I and at least one compound II. However, the composition may also be any combination of a compound I with at least one compound II, it not being required for compounds I and II to be present together in the same formulation.

An example of a composition according to the invention in which the compound I and the at least one compound II are not present together in the same formulation is a kit of parts. In a kit of parts, two or more components of a kit are packaged separately, i.e., not pre-formulated. As such, kits include one or more separate containers such as vials, cans, bottles, pouches, bags or canisters, each container containing a separate component for an agrochemical composition. One example is a two-component kit. Accordingly the present invention also relates to a two-component kit, comprising a first component which in turn comprises a compound I, a liquid or solid carrier and, if appropriate, at least one surfactant and/or at least one customary auxiliary, and a second component which in turn comprises at least one compound II, a liquid or solid carrier and, if appropriate, at least one surfactant and/or at least one customary auxiliary. Suitable liquid and solid carriers, surfactants and customary auxiliaries are described below.

The invention also refers to the use of a compound I in combination with at least a compound II according to the definition given above or below for controlling phytopathogenic fungi and to a method for controlling phytopathogenic fungi, comprising treating the fungi, their habitat or the seed, the soil or the plants to be protected against fungal attack with an effective amount of the compound I and the compound II according to the definition given above or below. The "combined" use of the compound I with and at least one compound II or the treatment according to the invention with an effective amount of the compound I and the compound II on the one hand can be understood as using a physical mixture of a compound I and at least one compound II. On the other hand, the combined use may also consist in using the compound I and the at least one compound II separately, but within a sufficiently short time of one another so that the desired effect can take place. More detailed illustrations of the combined use can be found in the specifications below.

The active compounds I and/or II of the inventive compositions can be present in different crystal modifications, which may differ in biological activity.

Compounds of formula I are contained in WO 99/54307. Granular pesticidal formulations of compounds I are the subject of EP 1 652 429. EP 1 222 856 is directed to plant disease controlling compositions comprising an imide compound selected from procymidone, iprodione and vinclozolin and a pyrazolinone derivative of a chemical formula I as disclosed in EP 1 222 856 A1. JP 2002316902 is directed to certain compositions having plant blight-preventing activity comprising a pyrazolinone compound and a second active compound selected from fluazinam, fludioxinil, pyrimethanil, cyprodinil, diethofencarb, mepanipyrim, penthiopyrad and boscalid.

The compounds II, their preparation and their activity against harmful fungi is known (cf.: http://www.alanwood.net/pesticides/); these substances are commercially available and known, for example, from the references below.

benalaxyl, methyl N-(phenylacetyl)-N-(2,6-xylyl)-DL-alaninate (DE 29 03 612), metalaxyl, methyl N-(methoxyacetyl)-N-(2,6-xylyl)-DL-alaninate (GB 15 00 581);

ofurace, (RS)-α-(2-chloro-N-2,6-xylylacetamido)-γ-butyrolactone [CAS RN 58810-48-3];

oxadixyl; N-(2,6-dimethylphenyl)-2-methoxy-N-(2-oxo-3-oxazolidinyl)acetamide (GB 20 58 059);

aldimorph, "4-alkyl-2,5(or 2,6)-dimethylmorpholine", comprising 65-75% of 2,6-dimethylmorpholine and 25-35% of 2,5-dimethylmorpholine, comprising more than 85% of 4-dodecyl-2,5(or 2,6)-dimethylmorpholine, where "alkyl" also includes octyl, decyl, tetradecyl and hexadecyl, with a cis/trans ratio of 1:1 [CAS RN 91315-15-0];

dodine, 1-dodecylguanidinium acetate (Plant Dis. Rep., Vol. 41, p. 1029 (1957));

dodemorph, 4-cyclododecyl-2,6-dimethylmorpholine (DE 1198125);

fenpropimorph, (RS)-cis-4-[3-(4-tert-butylphenyl)-2-methylpropyl]-2,6-dimethylmorpholine (DE 27 52 096);

fenpropidin, (RS)-1-[3-(4-tert-butylphenyl)-2-methylpropyl]piperidine (DE 27 52 096);

guazatine, mixture of the reaction products from the amidation of technical grade iminodi(octamethylene)diamine, comprising various guanidines and polyamines [CAS RN 108173-90-6];

iminoctadine, 1,1'-iminodi(octamethylene)diguanidine (Congr. Plant Pathol., 1., p. 27 (1968);

spiroxamine, (8-tert-butyl-1,4-dioxaspiro[4.5]dec-2-yl)diethylamine (EP-A 281 842);

tridemorph, 2,6-dimethyl-4-tridecylmorpholine (DE 11 64 152);

pyrimethanil, 4,6-dimethylpyrimidin-2-ylphenylamine (DD-A 151 404);

mepanipyrim, (4-methyl-6-prop-1-ynylpyrimidin-2-yl)phenylamine (EP-A 224 339);

cyprodinil, (4-cyclopropyl-6-methylpyrimidin-2-yl)phenylamine (EP-A 310 550);

cycloheximid, 4-{(2R)-2-[(1S,3S,5S)-3,5-dimethyl-2-oxocyclohexyl]-2-hydroxyethyl}piperidine-2,6-dione [CAS RN 66-81-9];

griseofulvin, 7-chloro-2',4,6-trimethoxy-6'-methylspiro[benzofuran-2(3H),1'-cyclohex-2'-ene]-3,4'-dione [CAS RN 126-07-8];

kasugamycin, 3-O-[2-amino-4-[(carboxyliminomethyl)amino]-2,3,4,6-tetradeoxy-α-Darabino-hexopyranosyl]-D-chiro-inositol [CAS RN 6980-18-3];

natamycin, (8E,14E,16E,18E,20E)-(1R,3S,5R,7R,12R,22R,24S,25R,26S)-22(3-amino-3,6-dideoxy-β-D-mannopyranosyloxy)-1,3,26-trihydroxy-12-methyl-10-oxo-6,11,28-trioxatricyclo[22.3.1.0$^{5,7}$]octacosa-8,14,16,18,20-pentaene-25-carboxylic acid [CAS RN 7681-93-8];

polyoxin, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxyl-β-D-allofuranuronic acid [CAS RN 22976-86-9];

streptomycin, 1,1'-{1-L-(1,3,5/2,4,6)-4-[5-deoxy-2-O-(2-deoxy-2-methylamino-α-L-glucopyranosyl)-3-C-formyl-α-L-Iyxofuranosyloxy]-2,5,6-trihydroxycyclohex-1,3-ylene}diguanidine (J. Am. Chem. Soc. Vol. 69, p. 1234 (1947));

bitertanol, β-([1,1'-biphenyl]-4-yloxy)-α-(1,1-dimethylethyl)-1H-1,2,4-triazole-1-ethanol (DE 23 24 020), bromuconazole, 1-[[4-bromo-2-(2,4-dichlorophenyl)tetrahydro-2-furanyl]methyl]-1H-1,2,4-triazole (Proc. 1990 Br. Crop. Prot. Conf.—Pests Dis. Vol. 1, p. 459);

cyproconazole, 2-(4-chlorophenyl)-3-cyclopropyl-1-[1,2,4]triazol-1-ylbutan-2-ol (U.S. Pat. No. 4,664,696);

difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607);

diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575);

enilconazole (imazalil), 1-[2-(2,4-dichlorphenyl)-2-(2-propenyloxy)ethyl]-1H-imidazole (Fruits, 1973, Vol. 28, p. 545);

epoxiconazole, (2RS,3SR)-1-[3-(2-chlorophenyl)-2,3-epoxy-2-(4-fluorophenyl)propyl]-1H-1,2,4-triazole (EP-A 196 038);

fenbuconazole, α-[2-(4-chlorophenyl)ethyl]-α-phenyl-1H-1,2,4-triazole-1-propanenitrile (Proc. 1988 Br. Crop Prot. Conf.—Pests Dis. Vol. 1, p. 33);

fluquinconazole, 3-(2,4-dichlorophenyl)-6-fluoro-2-[1,2,4]-triazol-1-yl-3H-quinazolin-4-one (Proc. Br. Crop Prot. Conf.-Pests Dis., 5-3, 411 (1992));

flusilazole, 1-{[bis-(4-fluorophenyl)methylsilanyl]methyl}-1H-[1,2,4]triazole (Proc. Br. Crop Prot. Conf.-Pests Dis., 1, 413 (1984));

flutriafol, α-(2-fluorophenyl)-α-(4-fluorophenyl)-1H-1,2,4-triazole-1-ethanol (EP 15 756);

hexaconazole, 2-(2,4-dichlorophenyl)-1-[1,2,4]triazol-1-ylhexan-2-ol (CAS RN 79983-71-4);

ipconazole, 2-[(4-chlorophenyl)methyl]-5-(1-methylethyl)-1-(1H-1,2,4-triazol-1-yl-methyl)cyclopentanol (EP 267 778), metconazole, 5-(4-chlorobenzyl)-2,2-dimethyl-1-[1,2,4]triazol-1-ylmethylcyclopentanol (GB 857 383);

myclobutanil, 2-(4-chlorophenyl)-2-[1,2,4]triazol-1-ylmethylpentanenitrile (CAS RN 88671-89-0);

penconazole, 1-[2-(2,4-dichlorophenyl)pentyl]-1H-[1,2,4]triazole (Pesticide Manual, 12th Ed. (2000), S.712);

propiconazole, 1-[[2-(2,4-dichlorophenyl)-4-propyl-1,3-dioxolan-2-yl]methyl]-1H-1,2,4-triazole (BE 835 579);

prochloraz, N-(propyl-[2-(2,4,6-trichlorophenoxy)ethyl])imidazole-1-carboxamide (U.S. Pat. No. 3,991,071);

prothioconazole, 2-[2-(1-chlorocyclopropyl)-3-(2-chlorophenyl)-2-hydroxypropyl]-2,4-dihydro-[1,2,4]triazole-3-thione (WO 96/16048);

simeconazole, α-(4-fluorophenyl)-α-[(trimethylsilyl)methyl]-1H-1,2,4-triazole-1-ethanol [CAS RN 149508-90-7], tebuconazole, 1-(4-chlorophenyl)-4,4-dimethyl-3-[1,2,4]triazol-1-ylmethylpentan-3-ol (EP-A 40 345);

tetraconazole, 1-[2-(2,4-dichlorophenyl)-3-(1,1,2,2-tetrafluoroethoxy)propyl]-1H-1,2,4-triazole (EP 234 242);

triadimefon, 1-(4-chlorophenoxy)-3,3-dimethyl-1-(1H-1,2,4-triazol-1-yl)-2-butanone (BE 793 867);

triadimenol, β-(4-chlorophenoxy)-α-(1,1-dimethylethyl)-1H-1,2,4-triazole-1-ethanol (DE 23 24 010);

triflumizol, (4-chloro-2-trifluormethylphenyl)-(2-propoxy-1-[1,2,4]triazol-1-ylethyliden)-amine (JP-A 79/119 462);

triticonazole, (5E)-5-[(4-chlorophenyl)methylene]-2,2-dimethyl-1-(1H-1,2,4-triazol-1-ylmethyl)cyclopentanol (FR 26 41 277);

iprodione, N-isopropyl-3-(3,5-dichlorophenyl)-2,4-dioxoimidazolidine-1-carboxamide (GB 13 12 536);

myclozolin, (RS)-3-(3,5-dichlorophenyl)-5-methoxymethyl-5-methyl-1,3-oxazolidine-2,4-dione [CAS RN 54864-61-8];

procymidone, N-(3,5-dichlorophenyl)-1,2-dimethylcyclopropane-1,2-dicarboximide (U.S. Pat. No. 3,903,090);

vinclozolin, 3-(3,5-dichlorophenyl)-5-methyl-5-vinyloxazolidine-2,4-dione (DE-A 22 07 576);

ferbam, iron(3+) dimethyldithiocarbamate (U.S. Pat. No. 1,972,961);

nabam, disodium ethylenebis(dithiocarbamate) (U.S. Pat. No. 2,317,765);

maneb, manganese ethylenebis(dithiocarbamate) (U.S. Pat. No. 2,504,404);

mancozeb, manganese ethylenebis(dithiocarbamate) polymer complex zinc salt (GB 996 264);

metam, methyldithiocarbaminic acid (U.S. Pat. No. 2,791,605);

metiram, zinc ammoniate ethylenebis(dithiocarbamate) (U.S. Pat. No. 3,248,400); propineb, zinc propylenebis(dithiocarbamate) polymer (BE 611 960);

polycarbamate, bis(dimethylcarbamodithioato-κS,κS')[μ-[[1,2-ethanediylbis[carbamodithioato-κS,κS']](2-)]]di[zinc] [CAS RN 64440-88-6];

thiram, bis(dimethylthiocarbamoyl) disulfide (DE 642 532);

ziram, dimethyldithiocarbamate [CAS RN 137-30-4];

zineb, zinc ethylenebis(dithiocarbamate) (U.S. Pat. No. 2,457,674);

anilazine, 4,6-dichloro-N-(2-chlorophenyl)-1,3,5-triazine-2-amine (U.S. Pat. No. 2,720,480);

benomyl, N-butyl-2-acetylaminobenzoimidazole-1-carboxamide (U.S. Pat. No. 3,631,176);

boscalid, 2-chloro-N-(4'-chlorobiphenyl-2-yl)nicotinamide (EP-A 545 099);

carbendazim, methyl (1H-benzoimidazol-2-yl)carbamate (U.S. Pat. No. 3,657,443);

carboxin, 5,6-dihydro-2-methyl-N-phenyl-1,4-oxathiin-3-carboxamide (U.S. Pat. No. 3,249,499);

oxycarboxin, 5,6-dihydro-2-methyl-1,4-oxathiin-3-carboxanilide 4,4-dioxide (U.S. Pat. No. 3,399,214);

cyazofamid, 4-chloro-2-cyano-N,N-dimethyl-5-(4-methylphenyl)-1H-imidazole-1-sulfonamide (CAS RN 120116-88-3];

dazomet, 3,5-dimethyl-1,3,5-thiadiazinane-2-thione (Bull. Soc. Chim. Fr. Vol. 15, p. 891 (1897));

dithianon, 5,10-dioxo-5,10-dihydronaphtho[2,3-b][1,4]dithiin-2,3-dicarbonitrile (GB 857 383);

famoxadone, (RS)-3-anilino-5-methyl-5-(4-phenoxyphenyl)-1,3-oxazolidine-2,4-dione [CAS RN 131807-57-3];

fenamidone, (S)-1-anilino-4-methyl-2-methylthio-4-phenylimidazolin-5-one [CAS RN 161326-34-7];

fenarimol, α-(2-chlorophenyl)-α-(4-chlorophenyl)-5-pyrimidinemethanol (GB 12 18 623);

fuberidazole, 2-(2-furanyl)-1H-benzimidazole (DE 12 09 799);

flutolanil, α,α,α-trifluoro-3'-isopropoxy-o-toluanilide (JP 1104514);

furametpyr, 5-chloro-N-(1,3-dihydro-1,1,3-trimethyl-4-isobenzofuranyl)-1,3-dimethyl-1H-pyrazole-4-carboxamide [CAS RN 123572-88-3];

isoprothiolane, diisopropyl 1,3-dithiolan-2-ylidenemalonate (Proc. Insectic. Fungic. Conf. 8. Vol. 2, p. 715 (1975));

mepronil, 3'-isopropoxy-o-toluanilide (U.S. Pat. No. 3,937,840);

nuarimol, α-(2-chlorophenyl)-α-(4-fluorophenyl)-5-pyrimidinemethanol (GB 12 18 623); fluopicolide (picobenzamid), 2,6-dichloro-N-(3-chloro-5-trifluoromethylpyridin-2-ylmethyl)benzamide (WO 99/42447);

probenazole, 3-allyloxy-1,2-benzothiazole 1,1-dioxide (Agric. Biol. Chem. Vol. 37, p. 737 (1973));

proquinazid, 6-iodo-2-propoxy-3-propylquinazolin-4(3H)-one (WO 97/48684);

pyrifenox, 2',4'-dichloro-2-(3-pyridyl)acetophenone (EZ)-O-methyloxime (EP 49 854);

pyroquilon, 1,2,5,6-tetrahydropyrrolo[3,2,1-ij]quinolin-4-one (GB 139 43 373)

quinoxyfen, 5,7-dichloro-4-(4-fluorophenoxy)quinoline (U.S. Pat. No. 5,240,940);

silthiofam, N-allyl-4,5-dimethyl-2-(trimethylsilyl)thiophene-3-carboxamide [CAS RN 175217-20-6];

thiabendazole, 2-(1,3-thiazol-4-yl)benzimidazole (U.S. Pat. No. 3,017,415);

thifluzamide, 2',6'-dibromo-2-methyl-4'-trifluormethoxy-4-trifluormethyl-1,3-thiazole-5-carboxanilide [CAS RN 130000-40-7];

thiophanate-methyl, 1,2-phenylenebis(iminocarbonothioyl)bis(dimethylcarbamate) (DE-A 19 30 540);

tiadinil, 3'-chloro-4,4'-dimethyl-1,2,3-thiadiazole-5-carboxanilide [CAS RN 223580-51-6];

tricyclazole, 5-methyl-1,2,4-triazolo[3,4-b][1,3]benzothiazole [CAS RN 41814-78-2];

triforine, N,N-{piperazine-1,4-diylbis[(trichlormethyl)methylene]}diformamide (DE 19 01 421);

Bordeaux mixture, mixture of $CuSO_4 \times 3Cu(OH)_2 \times 3CaSO_4$ [CAS RN 8011-63-0] copper acetate, $Cu(OCOCH_3)_2$ [CAS RN 8011-63-0];

copper oxychloride, $Cu2Cl(OH)_3$ [CAS RN 1332-40-7];

basic copper sulfate, $CuSO_4$ [CAS RN 1344-73-6];

binapacryl, (RS)-2-sec-butyl-4,6-dinitrophenyl 3-methylcrotonate [CAS RN 485-31-4];

dinocap, the mixture of 2,6-dinitro-4-octylphenylcrotonate and 2,4-dinitro-6-octylphenylcrotonate, where "octyl" is a mixture of 1-methylheptyl, 1-ethylhexyl and 1-propylpentyl (U.S. Pat. No. 2,526,660);

dinobuton, (RS)-2-sec-butyl-4,6-dinitrophenyl isopropyl carbonate [CAS RN 973-21-7];

nitrothal-isopropyl, diisopropyl 5-nitroisophthalate (Proc. Br. Insectic. Fungic. Conf. 7., Vol. 2, p. 673 (1973));

fenpiclonil, 4-(2,3-dichlorophenyl)-1H-pyrrole-3-carbonitrile (Proc. 1988 Br. Crop Prot. Conf.—Pests Dis., Vol. 1, p. 65);

fludioxonil, 4-(2,2-difluorobenzo[1,3]dioxol-4-yl)-1H-pyrrole-3-carbonitrile (The Pesticide Manual, publ. The British Crop Protection Council, 10th ed. (1995), p. 482);

acibenzolar-S-methyl, methyl 1,2,3-benzothiadiazol-7-carbothioate [CAS RN 135158-54-2];

flubenthiavalicarb (benthiavalicarb), isopropyl {(S)-1-[(1R)-1-(6-fluorobenzothiazol-2-yl)-ethylcarbamoyl]-2-methylpropyl}carbamate (JP-A 09/323,984);

carpropamid, 2,2-dichloro-N-[1-(4-chlorphenyl)ethyl]-1-ethyl-3-methylcyclopropane-carboxamide [CAS RN 104030-54-8];

chlorothalonil, 2,4,5,6-tetrachloroisophthalonitrile (U.S. Pat. No. 3,290,353);

cyflufenamid, (Z)-N-[α-(cyclopropylmethoxyimino)-2,3-difluoro-6-(trifluoromethyl)benzyl]-2-phenylacetamide (WO 96/19442);

cymoxanil, 1-(2-cyano-2-methoxyiminoacetyl)-3-ethylurea (U.S. Pat. No. 3,957,847);

diclomezine, 6-(3,5-dichlorophenyl-p-tolyl)pyridazin-3(2H)-one (U.S. Pat. No. 4,052,395) diclocymet, (RS)-2-cyano-N—[(R)-1-(2,4-dichlorophenyl)ethyl]-3,3-dimethylbutyramide [CAS RN 139920-32-4];

diethofencarb, isopropyl 3,4-diethoxycarbanilate (EP 78 663);

edifenphos, O-ethyl S,S-diphenyl phosphorodithioate (DE 14 93 736) ethaboxam, N-(cyano-2-thienylmethyl)-4-ethyl-2-(ethylamino)-5-thiazolecarboxamide (EP-A 639 574);

fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327);

fentin acetate, triphenyltin (U.S. Pat. No. 3,499,086);

fenoxanil, N-(1-cyano-1,2-dimethylpropyl)-2-(2,4-dichlorophenoxy)propanamide (EP 262 393);

ferimzone, (Z)-2'-methylacetophenone-4,6-dimethylpyrimidin-2-ylhydrazone [CAS RN 89269-64-7];

fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474);

fosetyl, fosetyl-aluminum, ethylphosphonate (FR 22 54 276);

iprovalicarb, isopropyl [(1S)-2-methyl-1-(1-p-tolylethylcarbamoyl)propyl]carbamate (EP-A 472 996);

hexachlorbenzene (C. R. Seances Acad. Agric. Fr., Vol. 31, p. 24 (1945));

metrafenon, 3'-bromo-2,3,4,6'-tetramethoxy-2',6-dimethylbenzophenone (U.S. Pat. No. 5,945,567);

pencycuron, 1-(4-chlorobenzyl)-1-cyclopentyl-3-phenylurea (DE 27 32 257);

penthiopyrad, (RS)-N-[2-(1,3-dimethylbutyl)-3-thienyl]-1-methyl-3-(trifluoromethyl)-1H-pyrazole-4-carboxamide (JP 10130268);

propamocarb, propyl 3-(dimethylamino)propylcarbamate (DE 15 67 169);

phthalide (DE 16 43 347);

toloclofos-methyl, O-2,6-dichloro-p-tolyl O,O-dimethyl phosphorothioate (GB 14 67 561);

quintozene, pentachlomitrobenzene (DE 682 048);

zoxamide, (RS)-3,5-dichloro-N-(3-chloro-1-ethyl-1-methyl-2-oxopropyl)-p-toluamide [CAS RN 156052-68-5];

azoxystrobin, methyl 2-{2-[6-(2-cyano-1-vinylpenta-1,3-dienyloxy)pyrimidin-4-yloxy]phenyl}-3-methoxyacrylate (EP 382 375), dimoxystrobin, (E)-2-(methoxyimino)-N-methyl-2-[α-(2,5-xylyloxy)-o-tolyl]acetamide (EP 477 631);

enestroburin, methyl 2-{2-[3-(4-chlorophenyl)-1-methylallylideneaminooxymethyl]-phenyl}-3-methoxyacrylate (EP 936 213);

fluoxastrobin, (E)-{2-[6-(2-chlorophenoxy)-5-fluoropyrimidin-4-yloxy]phenyl}(5,6-dihydro-1,4,2-dioxazin-3-yl)methanone O-methyloxime (WO 97/27189);

kresoxim-methyl, methyl (E)-methoxyimino[α-(o-tolyloxy)-o-tolyl]acetate (EP 253 213);

metominostrobin, (E)-2-(methoxyimino)-N-methyl-2-(2-phenoxyphenyl)acetamide (EP 398 692);

orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552); picoxystrobin, methyl 3-methoxy-2-[2-(6-trifluoromethylpyridin-2-yloxymethyl)phenyl]-acrylate (EP 278 595);
pyraclostrobin, methyl N-{2-[1-(4-chlorophenyl)-1H-pyrazol-3-yloxymethyl]phenyl}(N-methoxy)carbamate (WO 96/01256);
trifloxystrobin, methyl (E)-methoxyimino-{(E)-α-[1-(α,α,α-trifluoro-m-tolyl)ethylidene-aminooxy]-o-tolyl}acetate (EP 460 575);
captafol, N-(1,1,2,2-tetrachloroethylthio)cyclohex-4-ene-1,2-dicarboximide (Phytopathology, Vol. 52, p. 754 (1962));
captan, N-(trichloromethylthio)cyclohex-4-ene-1,2-dicarboximide (U.S. Pat. No. 2,553,770);
dichlofluanid, N-dichlorofluoromethylthio-N,N-dimethyl-N-phenylsulfamide (DE 11 93 498);
folpet, N-(trichlormethylthio)phthalimide (U.S. Pat. No. 2,553,770); tolylfluanid, N-dichlorofluoromethylthio-N,N-dimethyl-N-p-tolylsulfamide (DE 11 93 498);
dimethomorph, 3-(4-chlorophenyl)-3-(3,4-dimethoxyphenyl)-1-morpholin-4-yl-propenone (EP 120 321);
flumetover, 2-(3,4-dimethoxyphenyl)-N-ethyl-α,α,α-trifluoro-N-methyl-p-toluamide [AGROW no. 243, 22 (1995)];
flumorph, 3-(4-fluorophenyl)-3-(3,4-dimethoxyphenyl)-1-morpholin-4-ylpropenone (EP 860 438).

The compounds described by IUPAC nomenclature, their preparation and their fungi-cidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624).

In the inventive compositions, as compound I, the following compounds are preferred:
5-amino-3-oxo-2,3-dihydro-pyrazole of the formula Ia

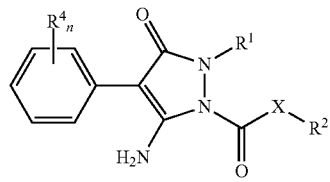

Ia wherein
$R^1$ is $C_1$-$C_6$-alkyl;
$R^2$ is $C_1$-$C_4$-alkyl, $C_3$-$C_4$-alkenyl or $C_3$-$C_4$-alkynyl;
$R^4$ is independently selected from the group consisting of $C_1$-$C_6$-alkyl, $C_2$-$C_4$-haloalkyl, $C_2$-$C_4$-alkenyl, $C_2$-$C_4$-alkynyl, $C_1$-$C_4$-alkoxy, $C_1$-$C_4$-haloalkoxy, $C_2$-$C_4$-alkenyloxy, $C_2$-$C_4$-alkynyloxy, $C_1$-$C_4$-alkylthio, cyano, nitro, F, Cl and Br;
n is 0, 1, 2, 3 or 4: and
X is O or S.

Thereby, it may be preferred according to the present invention that in formula Ia, $R^4$ is independently selected from the group consisting of $C_1$-$C_6$-alkyl, F, Cl and Br.
Furthermore, compounds of formular Ia are preferred, wherein
$R^1$ is 1-methylethyl, 1,1-dimethylethyl, 1-methylpropyl, 1-ethylpropyl or 1-methylbutyl;
$R^2$ is ethyl, n-propyl, allyl or propargyl;
$R^4$ is independently selected from the group consisting of F, Cl, Br, methyl, ethyl and isopropyl;
n is 0, 1, 2, 3 or 4: and
X is O or S.

According to one specific embodiment of the invention, in formula I or Ia, $R^1$ is 1-methylethyl or 1-methylpropyl.
According to another specific embodiment, in formula I or Ia, $R^2$ is allyl or ethyl.
According to another specific embodiment, $R^4$ is methyl or chlorine and n is 1 or 2.
According to another specific embodiment, in formula I or Ia, X is S.
According to still another specific embodiment, in formula I or Ia, X is O.
According to a preferred embodiment of the invention, the compound of formula I is 5-Amino-2-isopropyl-3-oxo-4-o-tolyl-2,3-dihydro-pyrazole-1-carbothioic acid S-allyl ester.
According to a further preferred embodiment of the invention, the compound of formula I is 5-Amino-2-sec-butyl-3-oxo-4-(2,6-dichlorophenyl)-2,3-dihydro-pyrazole-1-carbothioic acid ethyl ester.

In the definitions of the symbols given for formula I, collective terms were used which denote the following substituents:
halogen: fluorine, chlorine, bromine and iodine;
alkyl and the alkyl moieities in alkoxy, alkylcarbonyl, alkylthiocarbonyl, alkylcarbonyloxy, alkylthiocarbonyloxy, alkylamino, dialkylamino, alkylaminocarbonyl, dialkylaminocarbonyl, alkylaminothiocarbonyl, dialkylaminothiocarbonyl, alkylaminocarbonyloxy, dialkylaminocarbonyloxy, alkylaminothiocarbonyloxy, dialkylaminothiocarbonyloxy, alkylthio, alkylsulfinyl, alkylsulfonyl and the like: saturated straight-chain or branched hydrocarbon radicals having 1 to 2, 1 to 4, 1 to 6 or 1 to 8 carbon atoms. $C_1$-$C_2$-alkyl is methyl or ethyl. $C_1$-$C_4$-alkyl is additionally also, for example, propyl, isopropyl, butyl, 1-methylpropyl (sec-butyl), 2-methylpropyl (isobutyl) or 1,1-dimethylethyl (tert-butyl). $C_1$-$C_6$-alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-alkyl is additionally also, for example, heptyl, octyl, 2-ethylhexyl and positional isomers thereof.
haloalkyl: alkyl as mentioned above, where some or all of the hydrogen atoms in these groups may be replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chloro-difluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2- difluoroethyl, 2,2-dichloro-2-fluoroethyl, 2,2,2-trichloroethyl, pentafluoroethyl or 1,1,1-trifluoroprop-2-yl;

alkenyl and the alkenyl moieties in alkenyloxy, alkenylcarbonyl and the like: monounsaturated straight-chain or branched hydrocarbon radicals having 2 to 4, 2 to 6 or 3 to 4 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like;

haloalkenyl and the haloalkenyl moieties in haloalkenyloxy, haloalkenylcarbonyl and the like: alkenyl as mentioned above, where some or all of the hydrogen atoms in these groups may be replaced by halogen atoms as mentioned above, in particular fluorine, chlorine and bromine, for example chlorovinyl, chloroallyl and the like;

alkynyl and the alkynyl moieties in alkynyloxy, alkynylcarbonyl and the like: straight-chain or branched hydrocarbon groups having 2 to 4, 2 to 6 or 3 to 4 carbon atoms and one or two triple bonds in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

haloalkynyl and the haloalkynyl moieties in haloalkynyloxy, haloalkynylcarbonyl and the like: alkynyl as mentioned above, where some or all of the hydrogen atoms in these groups may be replaced by halogen atoms as mentioned above, in particular fluorine, chlorine and bromine;

alkoxy: an alkyl group attached via oxygen. $C_1$-$C_2$-alkoxy is methoxy or ethoxy. $C_1$-$C_4$-alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). $C_1$-$C_6$-alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

haloalkoxy: an alkoxy radical as mentioned above which is partially or fully substituted by fluorine, chlorine, bromine and/or iodine, preferably by fluorine. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

alkenyloxy: alkenyl as mentioned above which is attached via an oxygen atom, for example $C_3$-$C_6$-alkenyloxy, such as 1-propenyloxy, 2-propenyloxy, 1-methylethenyloxy, 1-butenyloxy, 2-butenyloxy, 3-butenyloxy, 1-methyl-1-propenyloxy, 2-methyl-1-propenyloxy, 1-methyl-2-propenyloxy, 2-methyl-2-propenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyl, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenyloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy and 1-ethyl-2-methyl-2-propenyloxy;

haloalkenyloxy: an alkenyloxy radical as mentioned above which is partially or fully substituted by fluorine, chlorine, bromine and/or iodine, preferably by fluorine.

alkynyloxy: alkynyl as mentioned above which is attached via an oxygen atom, for example $C_3$-$C_6$-alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy and the like;

haloalkynyloxy: an alkynyloxy radical as mentioned above which is partially or fully substituted by fluorine, chlorine, bromine and/or iodine, preferably by fluorine.

alkoxyalkyl: alkyl as defined above having 1 to 8, 1 to 6 or 1 to 4, in particular 1 to 3, carbon atoms, in which one hydrogen atom is replaced by an alkoxy group having 1 to 8, 1 to 6 or 1 to 4 carbon atoms, for example methoxymethyl, 2-methoxyethyl, ethoxymethyl, 3-methoxypropyl, 3-ethoxypropyl and the like.

alkylthio: alkyl as defined above which is attached via a sulfur atom.

haloalkylthio: haloalkyl as defined above which is attached via a sulfur atom.

According to one embodiment of the present invention, group B) of compounds II is as follows:

B) carboxamides
carboxanilides: benalaxyl, benalaxyl-M, benodanil, carboxin, fenfuram, fenhexamid, flutolanil, furametpyr, isopyrazam, isotianil, kiralaxyl, mepronil, metalaxyl, metalaxyl-M (mefenoxam), ofurace, oxadixyl, oxycarboxin, tecloftalam, thifluzamide, tiadinil, 2-amino-4-methyl-thiazole-5-carboxanilide, 2-chloro-N-(1,1,3-trimethyl-indan-4-yl)-nicotinamide, N-[2-(1,1,2,3,3,3-hexafluoropropoxy)-phenyl]-3-difluoromethyl-1-methyl-1H-pyrazole-4-carboxamide, N-[2-(1,1,2,2-tetrafluoroethoxy)-phenyl]-3-difluoromethyl-1-methyl-1H-pyrazole-4-carboxamide, N-(2-(1,3-dimethyl-butyl)-phenyl)-1,3-dimethyl-5-fluoro-1H-pyrazole-4-carboxamide, N-(2-(1,3,3-trimethyl-butyl)-phenyl)-1,3-dimethyl-5-fluoro-1H-pyrazole-4-carboxamide, N-(2-bicyclopropyl-2-yl-phenyl)-3-difluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoromethyl-1-methyl-1H-pyrazole-4-carboxamide, N-[1,2,3,4-tetrahydro-9-(1-methylethyl)-1,4-methanonaphthalen-5-yl]-3-(difluoromethyl)-1-methyl-1H-pyrazole-4-carboxamide;

carboxylic morpholides: dimethomorph, flumorph;

benzoic acid amides: flumetover, fluopicolde, fluopyram, zoxamide, N-(3-ethyl-3,5,5-trimethylcyclohexyl)-3-formylamino-2-hydroxybenzamide;

other carboxamides: carpropamid, dicyclomet, mandiproamid, oxytetracyclin, silthiofarm and N-(6-methoxy-pyridin-3-yl)cyclopropanecarboxylic acid amide;

According to the present invention, it may be preferred that the compositions comprise as compound II a compound that is selected from the group A), C), D), E), F) and G).

According to another embodiment of the invention, the compositions comprise as compound II a compound that is selected from the group H).

According to still another embodiment of the invention, the compositions comprise as compound II a compound that is selected from the group I).

According to the present invention, compositions comprising as compound II a compound of group A (strobilurins), in particular selected from pyraclostrobin, azoxystrobin, picoxystrobin, trifloxystrobin, enestroburin and pyribencarb, and specifically selected from pyraclostrobin, azoxystrobin and picoxystrobin, are preferred.

According to still another embodiment of the present invention, compositions comprising as compound II a compound of group B (carboxamides), in particular selected from isopyrazam, fluopicolide, fluopyram, mandiproamid, amisulbrom, flutolanil, mepronil, metalaxyl, oxadixyl, benalaxyl, ofurace, flumorph, dimethomorph, flumetover and fenhexamid, are preferred.

According to still another embodiment of the present invention, compositions comprising as compound II a compound of group C (azoles), in particular selected from benomyl, carbendazim, thiabendazole, simeconazole, imazalil, myclobutanil, bitertanol, metconazole, triflumizole, difenoconazole, triadimefon, flusilazole, triadimenol, tebuconazol, bromuconazole, cyproconazole and prothioconazole, are preferred.

According to still another embodiment of the present invention, compositions comprising as compound II a compound of group D (heterocyclic compounds), in particular selected from 3-[5-(4-Chloro-phenyl)-2,3-dimethyl-isoxazolidin-3-yl]-pyridine, famoxadone, fenamidone, fenarimol, nuarimol, bupirimate, folpet and captan, are preferred.

According to still another embodiment of the present invention, compositions comprising as compound II a compound of group E (carbamates), in particular selected from mancozeb, maneb, metiram, thiram, zineb, propineb, ziram, iprovalicarb, valiphenal and benthiavalicarb and specifically selected from propineb, are preferred.

According to still another embodiment of the present invention, compositions comprising as compound II a compound of group F (other active substances), in particular selected from cymoxanil, thiophanate-methyl, fosetyl, fosetyl-aluminum, chlorothalonil and dodine, and specifically selected from fosetyl, fosetyl-aluminum and chlorothalonil, are preferred.

Specific embodiments of the inventive compositions are the following synergistic compositions E1) to E64):

E1) Synergistic composition of 5-Amino-2-isopropyl-3-oxo-4-o-tolyl-2,3-dihydro-pyrazole-1-carbothioic acid S-allyl ester and pyraclostrobin.

E2) Synergistic composition of 5-Amino-2-isopropyl-3-oxo-4-o-tolyl-2,3-dihydro-pyrazole-1-carbothioic acid S-allyl ester and azoxystrobin.

E3) Synergistic composition of 5-Amino-2-isopropyl-3-oxo-4-o-tolyl-2,3-dihydro-pyrazole-1-carbothioic acid S-allyl ester and trifloxystrobin.

E4) Synergistic composition of 5-Amino-2-isopropyl-3-oxo-4-o-tolyl-2,3-dihydro-pyrazole-1-carbothioic acid S-allyl ester and enestroburin.

E5) Synergistic composition of 5-Amino-2-isopropyl-3-oxo-4-o-tolyl-2,3-dihydro-pyrazole-1-carbothioic acid S-allyl ester and pyribencarb.

E6) Synergistic composition of 5-Amino-2-isopropyl-3-oxo-4-o-tolyl-2,3-dihydro-pyrazole-1-carbothioic acid S-allyl ester and isopyrazam.

E7) Synergistic composition of 5-Amino-2-isopropyl-3-oxo-4-o-tolyl-2,3-dihydro-pyrazole-1-carbothioic acid S-allyl ester and fluopicolide.

E8) Synergistic composition of 5-Amino-2-isopropyl-3-oxo-4-o-tolyl-2,3-dihydro-pyrazole-1-carbothioic acid S-allyl ester and fluopyram.
E9) Synergistic composition of 5-Amino-2-isopropyl-3-oxo-4-o-tolyl-2,3-dihydro-pyrazole-1-carbothioic acid S-allyl ester and ethaboxam.
E10) Synergistic composition of 5-Amino-2-isopropyl-3-oxo-4-o-tolyl-2,3-dihydro-pyrazole-1-carbothioic acid S-allyl ester and mandipropamid.
E11) Synergistic composition of 5-Amino-2-isopropyl-3-oxo-4-o-tolyl-2,3-dihydro-pyrazole-1-carbothioic acid S-allyl ester and amisulbrom.
E12) Synergistic composition of 5-Amino-2-isopropyl-3-oxo-4-o-tolyl-2,3-dihydro-pyrazole-1-carbothioic acid S-allyl ester and 3-[5-(4-Chloro-phenyl)-2,3-dimethyl-isoxazolidin-3-yl]-pyridine.
E13) Synergistic composition of 5-Amino-2-isopropyl-3-oxo-4-o-tolyl-2,3-dihydro-pyrazole-1-carbothioic acid S-allyl ester and cyazofamid.
E14) Synergistic composition of 5-Amino-2-isopropyl-3-oxo-4-o-tolyl-2,3-dihydro-pyrazole-1-carbothioic acid S-allyl ester and famoxadone.
E15) Synergistic composition of 5-Amino-2-isopropyl-3-oxo-4-o-tolyl-2,3-dihydro-pyrazole-1-carbothioic acid S-allyl ester and fenamidone.
E16) Synergistic composition of 5-Amino-2-isopropyl-3-oxo-4-o-tolyl-2,3-dihydro-pyrazole-1-carbothioic acid S-allyl ester and mancozeb.
E17) Synergistic composition of 5-Amino-2-isopropyl-3-oxo-4-o-tolyl-2,3-dihydro-pyrazole-1-carbothioic acid S-allyl ester and maneb.
E18) Synergistic composition of 5-Amino-2-isopropyl-3-oxo-4-o-tolyl-2,3-dihydro-pyrazole-1-carbothioic acid S-allyl ester and metiram.
E19) Synergistic composition of 5-Amino-2-isopropyl-3-oxo-4-o-tolyl-2,3-dihydro-pyrazole-1-carbothioic acid S-allyl ester and thiram.
E20) Synergistic composition of 5-Amino-2-isopropyl-3-oxo-4-o-tolyl-2,3-dihydro-pyrazole-1-carbothioic acid S-allyl ester and zineb.
E21) Synergistic composition of 5-Amino-2-isopropyl-3-oxo-4-o-tolyl-2,3-dihydro-pyrazole-1-carbothioic acid S-allyl ester and propineb.
E22) Synergistic composition of 5-Amino-2-isopropyl-3-oxo-4-o-tolyl-2,3-dihydro-pyrazole-1-carbothioic acid S-allyl ester and ziram.
E23) Synergistic composition of 5-Amino-2-isopropyl-3-oxo-4-o-tolyl-2,3-dihydro-pyrazole-1-carbothioic acid S-allyl ester and flutolanil.
E24) Synergistic composition of 5-Amino-2-isopropyl-3-oxo-4-o-tolyl-2,3-dihydro-pyrazole-1-carbothioic acid S-allyl ester and mepronil.
E25) Synergistic composition of 5-Amino-2-isopropyl-3-oxo-4-o-tolyl-2,3-dihydro-pyrazole-1-carbothioic acid S-allyl ester and metalaxyl.
E26) Synergistic composition of 5-Amino-2-isopropyl-3-oxo-4-o-tolyl-2,3-dihydro-pyrazole-1-carbothioic acid S-allyl ester and oxadixyl.
E27) Synergistic composition of 5-Amino-2-isopropyl-3-oxo-4-o-tolyl-2,3-dihydro-pyrazole-1-carbothioic acid S-allyl ester and benalaxyl.
E28) Synergistic composition of 5-Amino-2-isopropyl-3-oxo-4-o-tolyl-2,3-dihydro-pyrazole-1-carbothioic acid S-allyl ester and ofurace.
E29) Synergistic composition of 5-Amino-2-isopropyl-3-oxo-4-o-tolyl-2,3-dihydro-pyrazole-1-carbothioic acid S-allyl ester and cymoxanil.
E30) Synergistic composition of 5-Amino-2-isopropyl-3-oxo-4-o-tolyl-2,3-dihydro-pyrazole-1-carbothioic acid S-allyl ester and benomyl.
E31) Synergistic composition of 5-Amino-2-isopropyl-3-oxo-4-o-tolyl-2,3-dihydro-pyrazole-1-carbothioic acid S-allyl ester and thiophanate-methyl.
E32) Synergistic composition of 5-Amino-2-isopropyl-3-oxo-4-o-tolyl-2,3-dihydro-pyrazole-1-carbothioic acid S-allyl ester and carbendazim.
E33) Synergistic composition of 5-Amino-2-isopropyl-3-oxo-4-o-tolyl-2,3-dihydro-pyrazole-1-carbothioic acid S-allyl ester and thiabendazol.
E34) Synergistic composition of 5-Amino-2-isopropyl-3-oxo-4-o-tolyl-2,3-dihydro-pyrazole-1-carbothioic acid S-allyl ester and simeconazole.
E35) Synergistic composition of 5-Amino-2-isopropyl-3-oxo-4-o-tolyl-2,3-dihydro-pyrazole-1-carbothioic acid S-allyl ester and imazalil.
E36) Synergistic composition of 5-Amino-2-isopropyl-3-oxo-4-o-tolyl-2,3-dihydro-pyrazole-1-carbothioic acid S-allyl ester and fenarimol.
E37) Synergistic composition of 5-Amino-2-isopropyl-3-oxo-4-o-tolyl-2,3-dihydro-pyrazole-1-carbothioic acid S-allyl ester and myclobutanil.
E38) Synergistic composition of 5-Amino-2-isopropyl-3-oxo-4-o-tolyl-2,3-dihydro-pyrazole-1-carbothioic acid S-allyl ester and bitertanol.
E39) Synergistic composition of 5-Amino-2-isopropyl-3-oxo-4-o-tolyl-2,3-dihydro-pyrazole-1-carbothioic acid S-allyl ester and metconazol.
E40) Synergistic composition of 5-Amino-2-isopropyl-3-oxo-4-o-tolyl-2,3-dihydro-pyrazole-1-carbothioic acid S-allyl ester and triflumizole.
E41) Synergistic composition of 5-Amino-2-isopropyl-3-oxo-4-o-tolyl-2,3-dihydro-pyrazole-1-carbothioic acid S-allyl ester and nuarimol.
E42) Synergistic composition of 5-Amino-2-isopropyl-3-oxo-4-o-tolyl-2,3-dihydro-pyrazole-1-carbothioic acid S-allyl ester and difenoconazole.
E43) Synergistic composition of 5-Amino-2-isopropyl-3-oxo-4-o-tolyl-2,3-dihydro-pyrazole-1-carbothioic acid S-allyl ester and triadimefon.
E44) Synergistic composition of 5-Amino-2-isopropyl-3-oxo-4-o-tolyl-2,3-dihydro-pyrazole-1-carbothioic acid S-allyl ester and flusilazol.
E45) Synergistic composition of 5-Amino-2-isopropyl-3-oxo-4-o-tolyl-2,3-dihydro-pyrazole-1-carbothioic acid S-allyl ester and triadimenol.
E46) Synergistic composition of 5-Amino-2-isopropyl-3-oxo-4-o-tolyl-2,3-dihydro-pyrazole-1-carbothioic acid S-allyl ester and tebuconazol.
E47) Synergistic composition of 5-Amino-2-isopropyl-3-oxo-4-o-tolyl-2,3-dihydro-pyrazole-1-carbothioic acid S-allyl ester and bromuconazol.
E48) Synergistic composition of 5-Amino-2-isopropyl-3-oxo-4-o-tolyl-2,3-dihydro-pyrazole-1-carbothioic acid S-allyl ester and cyproconazol.
E49) Synergistic composition of 5-Amino-2-isopropyl-3-oxo-4-o-tolyl-2,3-dihydro-pyrazole-1-carbothioic acid S-allyl ester and prothioconazol.
E50) Synergistic composition of 5-Amino-2-isopropyl-3-oxo-4-o-tolyl-2,3-dihydro-pyrazole-1-carbothioic acid S-allyl ester and iprovalicarb.
E51) Synergistic composition of 5-Amino-2-isopropyl-3-oxo-4-o-tolyl-2,3-dihydro-pyrazole-1-carbothioic acid S-allyl ester and valiphenal.

E52) Synergistic composition of 5-Amino-2-isopropyl-3-oxo-4-o-tolyl-2,3-dihydro-pyrazole-1-carbothioic acid S-allyl ester and flumorph.

E53) Synergistic composition of 5-Amino-2-isopropyl-3-oxo-4-o-tolyl-2,3-dihydro-pyrazole-1-carbothioic acid S-allyl ester and dimethomorph.

E54) Synergistic composition of 5-Amino-2-isopropyl-3-oxo-4-o-tolyl-2,3-dihydro-pyrazole-1-carbothioic acid S-allyl ester and benthiavalicarb.

E55) Synergistic composition of 5-Amino-2-isopropyl-3-oxo-4-o-tolyl-2,3-dihydro-pyrazole-1-carbothioic acid S-allyl ester and flumetover.

E56) Synergistic composition of 5-Amino-2-isopropyl-3-oxo-4-o-tolyl-2,3-dihydro-pyrazole-1-carbothioic acid S-allyl ester and fenhexamid.

E57) Synergistic composition of 5-Amino-2-isopropyl-3-oxo-4-o-tolyl-2,3-dihydro-pyrazole-1-carbothioic acid S-allyl ester and zoxamide.

E58) Synergistic composition of 5-Amino-2-isopropyl-3-oxo-4-o-tolyl-2,3-dihydro-pyrazole-1-carbothioic acid S-allyl ester and ethaboxam.

E59) Synergistic composition of 5-Amino-2-isopropyl-3-oxo-4-o-tolyl-2,3-dihydro-pyrazole-1-carbothioic acid S-allyl ester and fosetyl.

E60) Synergistic composition of 5-Amino-2-isopropyl-3-oxo-4-o-tolyl-2,3-dihydro-pyrazole-1-carbothioic acid S-allyl ester and chlorothalonil.

E61) Synergistic composition of 5-Amino-2-isopropyl-3-oxo-4-o-tolyl-2,3-dihydro-pyrazole-1-carbothioic acid S-allyl ester and bupirimate.

E62) Synergistic composition of 5-Amino-2-isopropyl-3-oxo-4-o-tolyl-2,3-dihydro-pyrazole-1-carbothioic acid S-allyl ester and dodine.

E63) Synergistic composition of 5-Amino-2-isopropyl-3-oxo-4-o-tolyl-2,3-dihydro-pyrazole-1-carbothioic acid S-allyl ester and folpet.

E64) Synergistic composition of 5-Amino-2-isopropyl-3-oxo-4-o-tolyl-2,3-dihydro-pyrazole-1-carbothioic acid S-allyl ester and captan.

A further aspect of the present invention is a composition, comprising 1) as compound I 5-Amino-2-isopropyl-3-oxo-4-o-tolyl-2,3-dihydro-pyrazole-1-carbothioic acid S-allyl ester and 2) at least one active compound II selected from procymidone, iprodione and vinclozolin in a synergistically effective amount.

In still a further aspect the present invention relates to a composition, comprising 1) as compound I 5-Amino-2-isopropyl-3-oxo-4-o-tolyl-2,3-dihydro-pyrazole-1-carbothioic acid S-allyl ester and 2) at least one active compound II selected from fluazinam, fludioxinil, pyrimethanil, cyprodinil, diethofencarb, mepanipyrim, penthiopyrad and boscalid, and specifically selected from cyprodinil, in a synergistically effective amount.

The compositions according to the invention are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. Fungi imperfecti). Some are systemically effective and they can be used in crop protection as foliar fungicides, fungicides for seed dressing and soil fungicides. Moreover, they are suitable for controlling harmful fungi, which inter alia occur in wood or roots of plants.

The compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; natural rubber plants or ornamental and forestry plants, such as flowers, shrubs, broad-leaved trees or evergreens, e.g. conifers; and on the plant propagation material, such as seeds, and the crop material of these plants.

Preferably the inventive compositions are used for controlling a multitude of fungi on field crops, such as potatoes, sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with the inventive combination of compounds I and compounds II and compositions thereof, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp).

Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinatetolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (*Coleoptera*), two-winged insects (*Diptera*), and moths (*Lepidoptera*) and to nematodes (*Nematoda*). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The inventive compositions are particularly suitable for controlling the following plant diseases:

*Albugo* spp. (white rust) on ornamentals, vegetables (e.g. *A. candida*) and sunflowers (e.g. *A. tragopogonis*);

*Alternaria* spp. (Alternaria leaf spot) on vegetables, rape (*A. brassicola* or brassi-cae), sugar beets (*A. tenuis*), fruits, rice, soybeans, potatoes (e.g. *A. solani* or *A. alternate*), tomatoes (e.g. *A. solani* or *A. alternate*) and wheat;

*Aphanomyces* spp. on sugar beets and vegetables;

*Ascochyta* spp. on cereals and vegetables, e.g. *A. tritici* (anthracnose) on wheat and *A. hordei* on barley;

*Bipolaris* and *Drechslera* spp. (teleomorph: *Cochliobolus* spp.) on corn (e.g. *D. maydis*), cereals (e.g. *B. sorokiniana*: spot blotch), rice (e.g. *B. oryzae*) and turfs;

Blumeria (formerly *Erysiphe*) *graminis* (powdery mildew) on cereals (e.g. on wheat or barley);

*Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat;

*Bremia lactucae* (downy mildew) on lettuce;

*Ceratocystis* (syn. *Ophiostoma*) spp. (rot or wilt) on broad-leaved trees and evergreens, e.g. *C. ulmi* (Dutch elm disease) on elms;

*Cercospora* spp. (Cercospora leaf spots) on corn, rice, sugar beets (e.g. *C. beticola*), sugar cane, vegetables, coffee, soybeans (e.g. *C. sojina* or *C. kikuchii*) and rice;

*Cladosporium* spp. on tomatoes (e.g. *C. fulvum*: leaf mold) and cereals, e.g. *C. herbarum* (black ear) on wheat;

*Claviceps purpurea* (ergot) on cereals;

*Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*);

*Colletotrichum* (teleomorph: *Glomerella*) spp. (anthracnose) on cotton (e.g. *C. gossypii*), corn (e.g. *C. graminicola*), soft fruits, potatoes (e.g. *C. coccodes*: black dot), beans (e.g. *C. lindemuthianum*) and soybeans (e.g. *C. truncatum* or *C. gloeosporioides*);

*Corticium* spp., e.g. *C. sasakii* (sheath blight) on rice;

*Corynespora cassiicola* (leaf spots) on soybeans and ornamentals;

*Cycloconium* spp., e.g. *C. oleaginum* on olive trees;

*Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals;

*Dematophora* (teleomorph: *Rosellinia*) necatrix (root and stem rot) on soybeans; *Diaporthe* spp., e.g. *D. phaseolorum* (damping off) on soybeans;

*Drechslera* (syn. *Helminthosporium*, teleomorph: *Pyrenophora*) spp. on corn, cereals, such as barley (e.g. D. teres, net blotch) and wheat (e.g. *D. tritici-repentis*: tan spot), rice and turf;

Esca (dieback, apoplexy) on vines, caused by *Formitiporia* (syn. *Phellinus*) punctata, *F. mediterranea, Phaeomoniella chlamydospora* (earlier *Phaeoacremonium chlamydosporum*), *Phaeoacremonium aleophilum* and/or *Botryosphaeria* obtuse; *Elsinoe* spp. on pome fruits (*E. pyri*), soft fruits (*E. veneta*: anthracnose) and vines (*E. ampeline*: anthracnose);

*Entyloma oryzae* (leaf smut) on rice;

*Epicoccum* spp. (black mold) on wheat;

*Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*);

*Eutypa lata* (Eutypa canker or dieback, anamorph: *Cytosporina lata*, syn. *Libertella blepharis*) on fruit trees, vines and ornamental woods;

*Exserohilum* (syn. *Helminthosporium*) spp. on corn (e.g. *E. turcicum*);

*Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn;

*Gaeumannomyces graminis* (take-all) on cereals (e.g. wheat or barley) and corn;

*Gibberella* spp. on cereals (e.g. *G. zeae*) and rice (e.g. *G. fujikuroi*: Bakanae disease);

*Glomerella cingulata* on vines, pome fruits and other plants and *G. gossypii* on cotton;

Grainstaining complex on rice;

*Guignardia bidwellii* (black rot) on vines;

*Gymnosporangium* spp. on rosaceous plants and junipers, e.g. *G. sabinae* (rust) on pears;

*Helminthosporium* spp. (syn. *Drechslera*, teleomorph: *Cochliobolus*) on corn, cereals and rice;

*Hemileia* spp., e.g. *H. vastatrix* (coffee leaf rust) on coffee;

*Isariopsis clavispora* (syn. *Cladosporium vitis*) on vines;

*Macrophomina phaseolina* (syn. phaseoli) (root and stem rot) on soybeans and cotton;

*Microdochium* (syn. *Fusarium*) nivale (pink snow mold) on cereals (e.g. wheat or barley);

*Microsphaera diffusa* (powdery mildew) on soybeans;

*Monilinia* spp., e.g. *M. taxa, M. fructicola* and *M. fructigena* (bloom and twig blight, brown rot) on stone fruits and other rosaceous plants;

*Mycosphaerella* spp. on cereals, bananas, soft fruits and ground nuts, such as e.g. *M. graminicola* (anamorph: *Septoria tritici, Septoria* blotch) on wheat or *M. fijiensis* (black Sigatoka disease) on bananas;

*Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*);

*Phakopsora pachyrhizi* and *P. meibomiae* (soybean rust) on soybeans;

*Phialophora* spp. e.g. on vines (e.g. *P. tracheiphila* and *P. tetraspora*) and soybeans (e.g. *P. gregata*: stem rot);

*Phoma lingam* (root and stem rot) on rape and cabbage and *P. betae* (root rot, leaf spot and damping-off) on sugar beets;

*Phomopsis* spp. on sunflowers, vines (e.g. *P. viticola*: can and leaf spot) and soybeans (e.g. stem rot: *P. phaseoli*, teleomorph: *Diaporthe* phaseolorum);

*Physoderma maydis* (brown spots) on corn;

*Phytophthora* spp. (wilt, root, leaf, fruit and stem root) on various plants, such as paprika and cucurbits (e.g. P. capsid), soybeans (e.g. *P. megasperma*, syn. *P. sojae*), potatoes and tomatoes (e.g. *P. infestans*: late blight) and broad-leaved trees (e.g. *P. ramorum*: sudden oak death);

*Plasmodiophora brassicae* (club root) on cabbage, rape, radish and other plants; *Plasmopara* spp., e.g. *P. viticola* (grapevine downy mildew) on vines and *P. halstedii* on sunflowers;

*Podosphaera* spp. (powdery mildew) on rosaceous plants, hop, pome and soft fruits, e.g. *P. leucotricha* on apples;

*Polymyxa* spp., e.g. on cereals, such as barley and wheat (*P. graminis*) and sugar beets (*P. betae*) and thereby transmitted viral diseases;

*Pseudocercosporella herpotrichoides* (eyespot, teleomorph: *Tapesia yallundae*) on cereals, e.g. wheat or barley;

*Pseudoperonospora* (downy mildew) on various plants, e.g. *P. cubensis* on cucurbits or *P. humili* on hop;

*Pseudopezicula tracheiphila* (red fire disease or, rotbrenner', anamorph: *Phialophora*) on vines;

*Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*);

*Pyrenophora* (anamorph: *Drechslera*) tritici-repentis (tan spot) on wheat or *P. teres* (net blotch) on barley;

*Pyricularia* spp., e.g. *P. oryzae* (teleomorph: *Magnaporthe grisea*, rice blast) on rice and *P. grisea* on turf and cereals;

*Pythium* spp. (damping-off) on turf, rice, corn, wheat, cotton, rape, sunflowers, soybeans, sugar beets, vegetables and various other plants (e.g. *P. ultimum* or *P. aphanidermatum*);

*Ramularia* spp., e.g. *R. collo-cygni* (Ramularia leaf spots, Physiological leaf spots) on barley and R. beticola on sugar beets;

*Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (Rhizoctonia spring blight) on wheat or barley;

*Rhizopus stolonifer* (black mold, soft rot) on strawberries, carrots, cabbage, vines and tomatoes;

*Rhynchosporium secalis* (scald) on barley, rye and triticale;

*Sarocladium oryzae* and *S. attenuatum* (sheath rot) on rice;

*Sclerotinia* spp. (stem rot or white mold) on vegetables and field crops, such as rape, sunflowers (e.g. *S. sclerotiorum*) and soybeans (e.g. *S. rolfsii* or *S. sclerotiorum*);

*Septoria* spp. on various plants, e.g. *S. glycines* (brown spot) on soybeans, *S. tritici* (Septoria blotch) on wheat and *S.* (syn. *Stagonospora*) *nodorum* (*Stagonospora blotch*) on cereals;

*Uncinula* (syn. *Erysiphe*) *necator* (powdery mildew, anamorph: *Oidium tuckeri*) on vines;

*Setospaeria* spp. (leaf blight) on corn (e.g. *S. turcicum*, syn. *Helminthosporium turcicum*) and turf;

*Sphacelotheca* spp. (smut) on corn, (e.g. *S. reiliana*: head smut), sorghum and sugar cane;

*Sphaerotheca fuliginea* (powdery mildew) on cucurbits;

*Spongospora subterranea* (powdery scab) on potatoes and thereby transmitted viral diseases;

*Stagonospora* spp. on cereals, e.g. *S. nodorum* (Stagonospora blotch, teleomorph: *Leptosphaeria* [syn. *Phaeosphaeria] nodorum*) on wheat;

*Synchytrium endobioticum* on potatoes (potato wart disease);

*Taphrina* spp., e.g. *T. deformans* (leaf curl disease) on peaches and *T. pruni* (plum pocket) on plums;

*Thielaviopsis* spp. (black root rot) on tobacco, pome fruits, vegetables, soybeans and cotton, e.g. *T. basicola* (syn. *Chalara elegans*);

*Tilletia* spp. (common bunt or stinking smut) on cereals, such as e.g. *T. tritici* (syn. *T. caries*, wheat bunt) and *T. controversa* (dwarf bunt) on wheat;

*Typhula incarnata* (grey snow mold) on barley or wheat;

*Urocystis* spp., e.g. *U. occulta* (stem smut) on rye;

*Uromyces* spp. (rust) on vegetables, such as beans (e.g. *U. appendiculatus*, syn. *U. phaseoli*) and sugar beets (e.g. *U. betae*); *Ustilago* spp. (loose smut) on cereals (e.g. *U. nuda* and *U. avaenae*), corn (e.g. *U. maydis*: corn smut) and sugar cane;

*Venturia* spp. (scab) on apples (e.g. *V. inaequalis*) and pears; and

*Verticillium* spp. (wilt) on various plants, such as fruits and ornamentals, vines, soft fruits, vegetables and field crops, e.g. *V. dahliae* on strawberries, rape, potatoes and tomatoes.

The inventive compositions are also suitable for controlling harmful fungi in the protection of materials (e.g. wood, paper, paint dispersions, fiber or fabrics) and in the protection of stored products. As to the protection of wood and construction materials, the particular attention is paid to the following harmful fungi: Ascomycetes such as *Ophiostoma* spp., *Ceratocystis* spp., *Aureobasidium pullulans, Sclerophoma* spp., *Chaetomium* spp., *Humicola* spp., Petrie*lla* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., *Deuteromycetes such as Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products the following yeast fungi are worthy of note: *Candida* spp. and *Saccharomyces cerevisae*.

In particular, the compositions of the present invention are effective against plant pathogens in speciality crops such as vine, fruits, hop, vegetables and tabacco—see the above list.

Plant propagation materials may be treated with the compositions of the invention prophylactically either at or before planting or transplanting.

The present invention also relates to a pesticidal agent comprising at least one solid or liquid carrier and a composition as described herein.

The compounds I and compounds II, their N-oxides and salts can be converted into customary types of agrochemical compositions, e.g. solutions, emulsions, suspensions, dusts, powders, pastes and granules. The composition type depends on the particular intended purpose; in each case, it should ensure a fine and uniform distribution of the compound according to the invention.

Examples for composition types are suspensions (SC, OD, FS), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF).

Usually the composition types (e.g. SC, OD, FS, WG, SG, WP, SP, SS, WS, GF) are employed diluted. Composition types such as DP, DS, GR, FG, GG and MG are usually used undiluted.

The compositions are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. Nos. 4,172,714, 4,144,050, 3,920, 442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical compositions may also comprise auxiliaries which are customary in agrochemical compositions. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wtters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkyl-arylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formal-dehyde, polyoxy-ethylene octylphenyl ether, ethoxylated isooctylphenol, octylphenol, nonylphenol, alkylphenol polyglycol ethers, tributylphenyl polyglycol ether, tristearyl-phenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinyl-amines (Lupasol® types, BASF, Germany), polyvinylpyrrolidone and the copolymers thereof.

Examples for thickeners (i.e. compounds that impart a modified flowability to compositions, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R.T. Vanderbilt, U.S.A.) or Attaclay® (Engelhard Corp., NJ, USA).

Bactericides may be added for preservation and stabilization of the composition. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds I and compounds II with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples for Composition Types are:
1. Composition Types for Dilution with Water
   i) Water-soluble concentrates (SL, LS)
      10 parts by weight of active compound(s) are dissolved in 90 parts by weight of water or in a water-soluble solvent. As an alternative, wetting agents or other auxiliaries are added. The active substance dissolves upon dilution with water. In this way, a composition having a content of 10% by weight of active substance is obtained.
   ii) Dispersible Concentrates (DC)
      20 parts by weight of active compound(s) are dissolved in 70 parts by weight of cyclohexanone with addition of 10 parts by weight of a dispersant, e.g. polyvinylpyrrolidone. Dilution with water gives a dispersion. The active substance content is 20% by weight.
   iii) Emulsifiable Concentrates (EC)
      15 parts by weight of a of active compound(s) are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.
   iv) Emulsions (EW, EO, ES)
      25 parts by weight of a of active compound(s) are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.
   v) Suspensions (SC, OD, FS)
      In an agitated ball mill, 20 parts by weight of active compound(s) are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.
   vi) Water-Dispersible Granules and Water-Soluble Granules (WG, SG)
      50 parts by weight of active compound(s) are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.
   vii) Water-Dispersible Powders and Water-Soluble Powders (WP, SP, SS, WS)
      75 parts by weight of active compound(s) are ground in a rotor-stator mill with addition of 25 parts by weight of dispersants, wetting agents and silica gel. Dilution with water gives a stable dispersion or solution of the active substance. The active substance content of the composition is 75% by weight.
   viii) Gel (GF)
      In an agitated ball mill, 20 parts by weight of active compound(s) are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.
2. Composition Types to be Applied Undiluted
   ix) Dustable Powders (DP, DS)
      5 parts by weight of active compound(s) are ground finely and mixed intimately with 95 parts by weight of finely divided kaolin. This gives a dustable composition having an active substance content of 5% by weight.
   x) Granules (GR, FG, GG, MG)
      0.5 parts by weight of active compound(s) is ground finely and associated with 99.5 parts by weight of carriers. Current methods are extrusion, spray-drying or the fluidized bed. This gives granules to be applied undiluted having an active substance content of 0.5% by weight.
   xi) ULV Solutions (UL)
      10 parts by weight of active compound(s) are dissolved in 90 parts by weight of an organic solvent, e.g. xylene.

This gives a composition to be applied undiluted having an active substance content of 10% by weight.

The agrochemical compositions generally comprise between 0.01 and 95%, preferably between 0.1 and 90%, most preferably between 0.5 and 90%, by weight of active substance. The active substances are employed in a purity of from 90% to 100%, preferably from 95% to 100% (according to NMR spectrum).

Water-soluble concentrates (LS), flowable concentrates (FS), powders for dry treatment (DS), water-dispersible powders for slurry treatment (WS), water-soluble powders (SS), emulsions (ES) emulsifiable concentrates (EC) and gels (GF) are usually employed for the purposes of treatment of plant propagation materials, particularly seeds. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before sowing. Methods for applying or treating agrochemical compounds and compositions thereof, respectively, on to plant propagation material, especially seeds, are known in the art, and include dressing, coating, pelleting, dusting and soaking application methods of the propagation material. In a preferred embodiment, the compounds or the compositions thereof, respectively, are applied on to the plant propagation material by a method such that germination is not induced, e.g. by seed dressing, pelleting, coating and dusting.

In a preferred embodiment, a suspension-type (FS) composition is used for seed treatment. Typically, a FS composition may comprise 1-800 g/l of active substance, 1-200 g/l Surfactant, 0 to 200 g/l antifreezing agent, 0 to 400 g/l of binder, 0 to 200 g/l of a pigment and up to 1 liter of a solvent, preferably water.

The active substances can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the active substances according to the invention.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of active substance.

The active substances may also be used successfully in the ultra-low-volume process (ULV), it being possible to apply compositions comprising over 95% by weight of active substance, or even to apply the active substance without additives.

When employed in plant protection, the amounts applied are, depending on the kind of effect desired, between 0.01 and 2.0 kg of active substance per ha.

In treatment of plant propagation materials such as seeds, e.g. by dusting, coating or drenching seed, amounts of active substance of from 1 to 1000 g, preferably from 5 to 100 g, per 100 kilogram of seed are generally required.

When used in the protection of materials or stored products, the amount of active substance applied depends on the kind of application area and on the desired effect. Amounts customarily applied in the protection of materials are, e.g., 0.001 g to 2 kg, preferably 0.005 g to 1 kg, of active substance per cubic meter of treated material.

Various types of oils, wetters, adjuvants, herbicides, bactericides, other fungicides and/or pesticides may be added to the active substances or the compositions comprising them, if appropriate not until immediately prior to use (tank mix). These agents can be admixed with the compositions according to the invention in a weight ratio of 1:100 to 100:1, preferably 1:10 to 10:1.

Adjuvants which can be used are in particular organic modified polysiloxanes such as Break Thru S 240®; alcohol alkoxylates such as Atplus 245®, Atplus MBA 1303®, Plurafac LF 300® and Lutensol ON 30®; EO/PO block polymers, e.g. Pluronic RPE 2035® and Genapol B®; alcohol ethoxylates such as Lutensol XP 80®; and dioctyl sulfosuccinate sodium such as Leophen RA®.

The compositions according to the invention can, in the use form as fungicides, also be present together with other active substances, e.g. with herbicides, insecticides, growth regulators, fungicides or else with fertilizers, as pre-mix or, if appropriate, not until immediately prior to use (tank mix).

According to this invention, applying the compounds I together with a compound II is to be understood to denote, that at least one compound I and at least one compound II occur simultaneously at the site of action (i.e. the harmful fungi to be controlled or their habitats such as infected plants, plant propagation materials, particularly seeds, surfaces, materials or the soil as well as plants, plant propagation materials, particularly seeds, soil, surfaces, materials or rooms to be protected from fungal attack) in an effective amount. This can be obtained by applying the compounds I and compound II simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In the compositions according to the invention the weight ratio of compound I and compound II generally depends from the properties of the active substances used, usually it is in the range of from 1:100 to 100:1, regularly in the range of from 1:50 to 50:1, preferably in the range of from 1:20 to 20:1 and particularly in the range of from 1:10 to 10:1. In a particularly preferred embodiment, compound I is present in at least equivalent amounts and preferably in excess. In this case, the weight ratio of compound I and compound II is preferably in the range of from 1:1 to 500:1, more preferably from 1.5:1 to 400:1, even more preferably from 2:1 to 300:1 and in particular from 3:1 to 300:1.

The components can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E.g., kits may include one or more fungicide component(s) and/or an adjuvant component and/or a insecticide component and/or a growth regulator component and/or a herbicde. One or more of the components may already be combined together or preformulated. In those embodiments where more than two components are provided in a kit, the components may already be combined together and as such are packaged in a single container such as a vial, bottle, can, pouch, bag or canister. In other embodiments, two or more components of a kit may be packaged separately, i.e., not preformulated. As such, kits may include one or more separate containers such as vials, cans, bottles, pouches, bags or canisters, each containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual components of the composition according to the invention such as parts of a kit or parts of a binary or ternary mixture may be mixed by the user himself in a spray tank and further auxiliaries may be added, if appropriate (tank mix).

In a further embodiment, either individual components of the composition according to the invention or partially pre-mixed components may be mixed by the user in a spray tank and further auxiliaries and additives may be added, if appropriate (tank mix).

In a further embodiment, either individual components of the composition according to the invention or partially pre-mixed components can be applied jointly (e.g. after tankmix) or consecutively.

The fungicidal action of the compositions according to the invention can be shown by the tests described below.

The active compounds, separately or jointly, are prepared as a stock solution comprising 25 mg of active compound which is made up to 10 ml using a mixture of acetone and/or DMSO and the emulsifier Uniperol® EL (wetting agent having an emulsifying and dispersing action based on ethoxylated alkylphenols) in a ratio by volume of solvent/emulsifier of 99:1. The mixture is then made up to 100 ml with water. This stock solution is diluted with the solvent/emulsifier/water mixture described to give the concentration of active compound stated below.

The visually determined percentages of infected leaf areas are converted into efficacies in % of the untreated control.

The efficacy (E) is calculated as follows using Abbot's formula:

$E=(1-\alpha/\beta) \cdot 100$

α corresponds to the fungicidal infection of the treated plants in % and
β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S.R. "Calculating synergistic and antagonistic responses of herbicide combinations", Weeds, 15, pp. 20-22, 1967) and compared with the observed efficacies.

Colby's formula: $E=x+y-x°y/100$

E expected efficacy, expressed in % of the untreated control, when using the mixture of the active compounds A and B at the concentrations a and b
x efficacy, expressed in % of the untreated control, when using the active compound A at the concentration a
y efficacy, expressed in % of the untreated control, when using the active compound B at the concentration b

EXAMPLES

Microtest

The active compounds were formulated separately or jointly as a stock solution having a concentration of 10000 ppm in dimethyl sulfoxide.

As compound I was used 5-amino-2-isopropyl-3-oxo-4-o-tolyl-2,3-dihydro-pyrazole-1-carbothioic acid ally ester of formula I.1

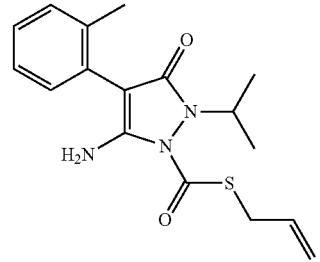

(I.1)

Use Example 1

Activity Against the Late Blight Pathogen
*Phytophthora infestans* in the Microtiter Test
(Phytin)

The stock solutions were pipetted onto a microtiter plate (MTP) and diluted with water to the stated concentrations. A spore suspension of *Phytophtora infestans* containing a pea juice-based aqueous nutrient medium was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds. These percentages were converted into efficacies. An efficacy of 0 means that the growth level of the pathogens corresponds to that of the untreated control; an efficacy of 100 means that the pathogens were not growing. The test results are shown in Table 1. The expected efficacies of active compound combinations were determined using Colby's formula (see above).

TABLE 1

| Active compound/ active mixture | Concentration [ppm] | Mixture | Observed efficacy [%] | Calculated efficacy[1] | Synergism [%] |
|---|---|---|---|---|---|
| I.1 | 63 | — | 37 | | |
| | 16 | — | 16 | | |

TABLE 1-continued

| Active compound/<br>active mixture | Concentration<br>[ppm] | Mixture | Observed<br>efficacy [%] | Calculated<br>efficacy[1] | Synergism<br>[%] |
|---|---|---|---|---|---|
| Azoxystrobin | 0.25 | — | 55 | | |
| Propineb | 1 | — | 21 | | |
| Fosetyl-Al | 16 | — | 35 | | |
| I.1 | 16 | 64:1 | 80 | 62 | 18 |
| Azoxystrobin | 0.25 | | | | |
| I.1 | 16 | 16:1 | 98 | 32 | 66 |
| Propineb | 1 | | | | |
| I.1 | 63 | 4:1 | 91 | 59 | 32 |
| Fosetyl-Al | 16 | | | | |

[1]according to Colby (%)

Use Example 2

Activity Against Leaf Blotch on wheat Caused by Septoria tritici in the Microtiter Test (Septtr)

The stock solutions were pipetted onto a microtiter plate (MTP) and diluted with water to the stated concentrations. A spore suspension of *Septoria tritici* in an aqueous biomalt solution was then added. The plates were placed in a water vapor-saturated chamber at temperatures of 18° C. Using an absorption photometer, the microtiter plates were measured at 405 nm on day 7 after the inoculation. The measured parameters were compared to the growth of the active compound-free control variant (100%) and the fungus-free and active compound-free blank value to determine the relative growth in % of the pathogens in the respective active compounds. These percentages were converted into efficacies. An efficacy of 0 means that the growth level of the pathogens corresponds to that of the untreated control; an efficacy of 100 means that the pathogens were not growing. The test results are shown in Table 2.

TABLE 2

| Active compound/<br>active mixture | Concentration<br>[ppm] | Mixture | Observed<br>efficacy [%] | Calculated<br>efficacy[1] | Synergism<br>[%] |
|---|---|---|---|---|---|
| I.1 | 4 | — | 37 | | |
| Azoxystrobin | 0.063 | — | 55 | | |
| Cyprodinil | 1 | — | 13 | | |
| Chlorothalonil | 0.25 | — | 46 | | |
| I.1 | 4 | 64:1 | 99 | 72 | 27 |
| Azoxystrobin | 0.063 | | | | |
| I.1 | 4 | 4:1 | 67 | 45 | 22 |
| Cyprodinil | 1 | | | | |
| I.1 | 4 | 16:1 | 90 | 66 | 24 |
| Chlorothalonil | 0.25 | | | | |

[1]according to Colby (%)

Use Example 3

Activity Against Pyrenophora teres in the Microtiter Test (Pyrnte)

The stock solutions were pipetted onto a microtiter plate (MTP) and diluted with water to the stated concentrations. A spore suspension of *Pyrenophora teres* in an aqueous biomalt solution was then added. The plates were placed in a water vapor-saturated chamber at temperatures of 18° C. Using an absorption photometer, the microtiter plates were measured at 405 nm on day 7 after the inoculation. The measured parameters were compared to the growth of the active compound-free control variant (100%) and the fungus-free and active compound-free blank value to determine the relative growth in % of the pathogens in the respective active compounds. These percentages were converted into efficacies. An efficacy of 0 means that the growth level of the pathogens corresponds to that of the untreated control; an efficacy of 100 means that the pathogens were not growing. The test results are shown in Table 3.

TABLE 3

| Active compound/<br>active mixture | Concentration<br>[ppm] | Mixture | Observed<br>efficacy [%] | Calculated<br>efficacy[1] | Synergism<br>[%] |
|---|---|---|---|---|---|
| I.1 | 1 | — | 34 | | |
| Picoxystrobin | 0.016 | — | 31 | | |
| I.1 | 1 | 64:1 | 72 | 54 | 18 |
| Picoxystrobin | 0.016 | | | | |

[1]according to Colby (%)

Use Example 4

Activity Against *Fusarium culmorum* in the Microtiter Test (Fusacu)

The stock solutions were pipetted onto a microtiter plate (MTP) and diluted with water to the stated concentrations. A spore suspension of *Fusarium culmorum* in an aqueous biomalt solution was then added. The plates were placed in a water vapor-saturated chamber at temperatures of 18° C. Using an absorption photometer, the microtiter plates were measured at 405 nm on day 7 after the inoculation. The measured parameters were compared to the growth of the active compound-free control variant (100%) and the fungus-free and active compound-free blank value to determine the relative growth in % of the pathogens in the respective active compounds. These percentages were converted into efficacies. An efficacy of 0 means that the growth level of the pathogens corresponds to that of the untreated control; an efficacy of 100 means that the pathogens were not growing. The test results are shown in Table 4.

TABLE 4

| Active compound/<br>active mixture | Concentration<br>[ppm] | Mixture | Observed<br>efficacy [%] | Calculated<br>efficacy[1] | Synergism<br>[%] |
|---|---|---|---|---|---|
| I.1 | 63 | — | 14 | | |
| Pyraclostrobin | 0.25 | — | 5 | | |
| I.1 | 63 | 250:1 | 41 | 18 | 23 |
| Pyraclostrobin | 0.25 | | | | |

[1]according to Colby (%)

The invention claimed is:

1. A composition, comprising
1) a 5-amino-3-oxo-2,3-dihydro-pyrazole compound I

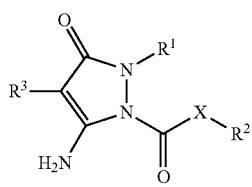

wherein
R$^1$ is C$_1$-C$_{10}$-alkyl;
R$^2$ is C$_1$-C$_6$-alkyl, C$_2$-C$_6$-alkenyl or C$_2$-C$_6$-alkynyl;
R$^3$ is phenyl, optionally substituted by one to five substituents independently selected from the group consisting of halogen, C$_1$-C$_6$-alkyl, C$_1$-C$_6$-haloalkyl, C$_2$-C$_6$-alkenyl, C$_2$-C$_6$-alkynyl, C$_1$-C$_6$-alkoxy, C$_1$-C$_6$-haloalkoxy, C$_2$-C$_6$-alkenyloxy, C$_2$-C$_6$-haloalkenyloxy, C$_2$-C$_6$-alkynyloxy, C$_2$-C$_6$-haloalkynyloxy, C$_1$-C$_6$-alkoxy-C$_1$-C$_6$-alkyl, C$_1$-C$_6$-alkoxy-C$_1$-C$_6$-alkoxy, C$_1$-C$_6$-alkylthio, C$_1$-C$_6$-haloalkylthio, C$_2$-C$_6$-alkenylthio, C$_2$-C$_6$-haloalkenylthio, cyano and nitro; and
X is or S;
and
2) at least one strobilurin compound selected from the group consisting of azoxystrobin, dimoxystrobin, enestroburin, fluoxastrobin, kresoxim-methyl, meto-minostrobin, orysastrobin, picoxystrobin, pyraclostrobin, pyribencarb, trifloxystrobin, 2-(2-(6-(3-chloro-2-methyl-phenoxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoyl-sulfanylmethyl)-phenyl)-acrylic acid methyl ester, methyl (2-chloro-5-[1-(3-methylbenzyl-oxyimino)ethyl]benzyl)carbamate and 2-(2-(3-(2,6-dichlorophenyl)-1-methyl-allylidene-aminooxymethyl)-phenyl)-2-methoxyimino-N-methyl-acetamide
in a synergistically effective amount.

2. The composition of claim 1, wherein in compounds I R$^1$ is C$_1$-C$_6$-alkyl; R$^2$ is C$_1$-C$_4$-alkyl, C$_3$-C$_4$-alkenyl or C$_3$-C$_4$-alkynyl; R$^3$ is phenyl, wherein the phenyl is unsubstituted or substituted by one to four substituents independently selected from the group consisting of C$_1$-C$_6$-alkyl, F, Cl and Br; and X is O or S.

3. The composition of claim 1, wherein in compounds I R$^1$ is 1-methylethyl, 1,1-dimethylethyl, 1-methylpropyl, 1-ethylpropyl or 1-methylbutyl; R$^2$ is ethyl, n-propyl, allyl or propargyl; R$^3$ is phenyl, wherein the phenyl is unsubstituted or substituted by one to four substituents independently selected from the group consisting of methyl, ethyl, isopropyl, F, Cl and Br; and X is O or S.

4. The composition of claim 1, wherein the compound of formula I is 5-Amino-2-isopropyl-3-oxo-4-o-tolyl-2,3-dihydro-pyrazole-1-carbothioic acid S-allyl ester.

5. A pesticidal agent comprising at least one solid or liquid carrier and a composition according to claim 1.

6. A seed treated with the composition of claim 1 in an amount of from 1 g to 1000 g per 100 kg of seed.

7. The seed of claim 6, wherein in compounds I R$^1$ is C$_1$-C$_6$-alkyl; R$^2$ is C$_1$-C$_4$-alkyl, C$_3$-C$_4$-alkenyl or C$_3$-C$_4$-alkynyl; R$^3$ is phenyl, wherein the phenyl is unsubstituted or substituted by one to four substituents independently selected from the group consisting of C$_1$-C$_6$-alkyl, F, Cl and Br; and X is O or S.

8. The seed of claim 6, wherein in compounds I R$^1$ is 1-methylethyl, 1,1-dimethylethyl, 1-methylpropyl, 1-ethylpropyl or 1-methylbutyl; R$^2$ is ethyl, n-propyl, allyl or propargyl; R$^3$ is phenyl, wherein the phenyl is unsubstituted or substituted by one to four substituents independently selected from the group consisting of methyl, ethyl, isopropyl, F, Cl and Br; and X is O or S.

9. The seed of claim 6, wherein the compound of formula I is 5-Amino-2-isopropyl-3-oxo-4-o-tolyl-2,3-dihydro-pyrazole-1-carbothioic acid S-allyl ester.

10. A method for controlling phytopathogenic harmful fungi, comprising treating the fungi, their habitat or the seed, the soil or the plants to be protected against fungal attack with an effective amount of compound I

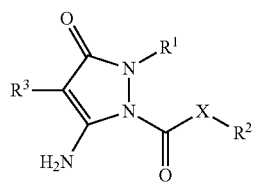

wherein
R$^1$ is C$_1$-C$_{10}$-alkyl;

$R^2$ is $C_1$-$C_6$-alkyl, $C_2$-$C_6$-alkenyl or $C_2$-$C_6$-alkynyl;

$R^3$ is phenyl, optionally substituted by one to five substituents independently selected from the group consisting of halogen, $C_1$-$C_6$-alkyl, $C_1$-$C_6$-haloalkyl, $C_2$-$C_6$-alkenyl, $C_2$-$C_6$-alkynyl, $C_1$-$C_6$-alkoxy, $C_1$-$C_6$-haloalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_1$-$C_6$-alkoxy-$C_1$-$C_6$-alkyl, $C_1$-$C_6$-alkoxy-$C_1$-$C_6$-alkoxy, $C_1$-$C_6$-alkylthio, $C_1$-$C_6$-haloalkylthio, $C_2$-$C_6$-alkenylthio, $C_2$-$C_6$-haloalkenylthio, cyano and nitro; and X is O or S;

and at least one strobilurin compound selected from the group consisting of azoxystrobin, dimoxystrobin, enestroburin, fluoxastrobin, kresoxim-methyl, metominostrobin, orysastrobin, picoxystrobin, pyraclostrobin, pyribencarb, trifloxystrobin, 2-(2-(6-(3-chloro-2-methyl-phen-oxy)-5-fluoro-pyrimidin-4-yloxy)-phenyl)-2-methoxyimino-N-methyl-acetamide, 3-methoxy-2-(2-(N-(4-methoxy-phenyl)-cyclopropane-carboximidoylsulfanylmethyl)-phenyl)-acrylic acid methyl ester, methyl (2-chloro-5-[1-(3-methylbenzyloxyimino)ethyl]benzyl)carbamate and 2-(2-(3-(2,6-dichlorophenyl)-1-methyl-allylideneaminooxymethyl)-phenyl)-2-methoxyimino-N-methyl-acetamide.

11. The method claim 10, wherein compound I and the strobilurin compound are applied jointly, simultaneously, separately or in succession.

12. The method of claim 10, wherein compound I and the strobilurin compound are applied in an amount of from 5 g/ha to 2500 g/ha.

13. The method of claim 10, wherein compound I and the strobilurin compound are applied in an amount of from 1 g to 1000 g per 100 kg of seed.

14. The method of claim 13, wherein in compounds I $R^1$ is $C_1$-$C_6$-alkyl; $R^2$ is $C_1$-$C_4$-alkyl, $C_3$-$C_4$-alkenyl or $C_3$-$C_4$-alkynyl; $R^3$ is phenyl, wherein the phenyl is unsubstituted or substituted by one to four substituents independently selected from the group consisting of $C_1$-$C_6$-alkyl, F, Cl and Br; and X is O or S.

15. The method of claim 13, wherein in compounds I $R^1$ is 1-methylethyl, 1,1-dimethylethyl, 1-methylpropyl, 1-ethylpropyl or 1-methylbutyl; $R^2$ is ethyl, n-propyl, allyl or prorargyl; $R^3$ is phenyl, wherein the phenyl is unsubstituted or substituted by one to four substituents independently selected from the group consisting of methyl, ethyl, isopropyl, F, Cl, and Br; and X is O or S.

16. The method of claim 13, wherein the compound of formula I is 5-Amino-2-isopropyl-3-oxo-4-o-tolyl-2,3-dihydro-pyrazole-1-carbothioic acid S-allyl ester.

* * * * *